US010987356B2

(12) United States Patent
Zhao et al.

(10) Patent No.: US 10,987,356 B2
(45) Date of Patent: Apr. 27, 2021

(54) DUAL INHIBITION OF CDK AND HSP90 DESTABILIZE H1F1 α AND SYNERGISTICALLY INDUCES CANCER CELL DEATH

(71) Applicant: Institute For Cancer Research, Philadelphia, PA (US)

(72) Inventors: Shuai Zhao, Philadelphia, PA (US); Wafik S. El-Deiry, Philadelphia, PA (US)

(73) Assignee: Institute For Cancer Research, Philadelphia, PA (US)

( * ) Notice: Subject to any disclaimer, the term of this patent is extended or adjusted under 35 U.S.C. 154(b) by 0 days.

(21) Appl. No.: 16/681,253

(22) Filed: Nov. 12, 2019

(65) Prior Publication Data
US 2020/0155554 A1 May 21, 2020

Related U.S. Application Data

(62) Division of application No. 15/904,935, filed on Feb. 26, 2018, now Pat. No. 10,729,692.

(60) Provisional application No. 62/463,666, filed on Feb. 26, 2017.

(51) Int. Cl.
*A61K 31/519* (2006.01)
*A61P 35/00* (2006.01)
*A61K 31/4196* (2006.01)

(52) U.S. Cl.
CPC ........ *A61K 31/519* (2013.01); *A61K 31/4196* (2013.01); *A61P 35/00* (2018.01)

(58) Field of Classification Search
CPC .................................... A61K 31/519
USPC ............... 514/80, 212.06, 218, 232.5, 235.2, 514/252.18, 254.08, 383
See application file for complete search history.

(56) References Cited

U.S. PATENT DOCUMENTS

| | | | |
|---|---|---|---|
| 6,316,456 B1 | 11/2001 | Meijer et al. | |
| 6,936,612 B2 | 8/2005 | Barvian et al. | |
| 7,855,211 B2 | 12/2010 | Coates et al. | |
| 8,383,619 B2 | 2/2013 | Williams et al. | |
| 8,906,885 B2 | 12/2014 | El-Hariry et al. | |

FOREIGN PATENT DOCUMENTS

WO   2010060937   6/2010

OTHER PUBLICATIONS

Fu et al., "Apoptosis of osteosarcoma cultures by the combination of the cyclin-dependent kinase inhibitor SCH727965 and a heat shock protein 90 inhibitor", Cell Death and Disease, vol. 4, e566, pp. 1-10 (2013).*
Calderwood, S. K., et al., "Heat Shock Proteins Promote Cancer: It's a Protection Racket", Trends Biochem Sci, 2016, 41(4), pp. 311-323.
Isaacs, J. S., et al., "Hsp90 Regulates a von Hippel Lindau-independent Hypoxia-inducible Factor-1α-degradative Pathway", J Biol Chem, 2002, 277(33), pp. 29936-29944.
Warfel, N. A., et al., "CDK1 stabilizes HIF-1α via direct phosphorylation of Ser668 to promote tumor growth", Cell Cycle, 2013, 12(23), pp. 3689-3701.

* cited by examiner

*Primary Examiner* — Kevin E Weddington
(74) *Attorney, Agent, or Firm* — Stadley Ronon Stevens & Young, LLP

(57) ABSTRACT

The present disclosure provides pharmaceutical compositions including a CDK inhibitor and an HSP90 inhibitor, as well as methods of treating cancer or a tumor in a subject by administering a CDK inhibitor and an HSP90 inhibitor to the subject.

19 Claims, 37 Drawing Sheets

CDK1 activity contributes to the interaction between HSP90 and HIF1α

| IP: HA-HIF1α | HCT116 | |
|---|---|---|
| transfected: HA-HIF1α | + | + |
| Ro-3306 | − | + |
| Blot: HSP90 |  | |
| Blot: HIF1α |  | |
| Input: HSP90 |  | |

Dual inhibition of CDK1 and HSP90 synergistically suppresses cell proliferation

| Ro3306 (µM) | Geldanamycin (µM) | Inhibitory effect | Combination index (CI) |
|---|---|---|---|
| 2.5 | 0.25 | 0.45 | 0.665 |
| 2.5 | 0.5 | 0.44 | 0.961 |
| 2.5 | 1 | 0.40 | 1.193 |
| 5 | 0.25 | 0.35 | 0.389 |
| 5 | 0.5 | 0.35 | 0.534 |
| 5 | 1 | 0.34 | 0.824 |
| 10 | 0.25 | 0.25 | 0.275 |
| 10 | 0.5 | 0.25 | 0.334 |
| 10 | 1 | 0.21 | 0.277 |

| Ro3306 (µM) | Geldanamycin (µM) | Inhibitory effect | Combination index (CI) |
| --- | --- | --- | --- |
| 2.5 | 1 | 0.89 | 1.293 |
| 2.5 | 2 | 0.77 | 0.903 |
| 2.5 | 4 | 0.69 | 1.086 |
| 5 | 1 | 0.74 | 0.479 |
| 5 | 2 | 0.63 | 0.473 |
| 5 | 4 | 0.64 | 0.891 |
| 10 | 1 | 0.34 | 0.131 |
| 10 | 2 | 0.33 | 0.171 |
| 10 | 4 | 0.32 | 0.248 |

C

Ro3306           +
Geldanamycin     + normoxia hypoxia

D ganetespib          -
palbociclib         - normoxia hypoxia

D

| ganetespib | − |
| palbociclib | + | normoxia hypoxia

D

A

Control

Palbociclib

Ganetespib

Palbociclib+
Ganetespib

B

A

B

DUAL INHIBITION OF CDK AND HSP90 DESTABILIZE H1F1 α AND SYNERGISTICALLY INDUCES CANCER CELL DEATH

CROSS-REFERENCE TO RELATED APPLICATIONS

This application claims priority to U.S. Application No. 62/463,666, filed Feb. 26, 2017, which is incorporated herein by reference in its entirety.

FIELD

The present disclosure is directed, in part, to compositions comprising a cyclin-dependent kinase inhibitor (CDKI) and a heat shock protein 90 (HSP90) inhibitor, and methods for treating cancer.

BACKGROUND

A prevalent characteristic of solid tumors is the presence of hypoxic areas. Intratumoral hypoxia plays a well-known role in chemo-/radio-therapy resistance and is associated with poor prognosis as well as enhanced metastasis. Hypoxia-inducible factor 1α (HIF1α) is a major mediator of the cellular response to hypoxia, which promotes malignant proliferation and progression in cancers. HIF-1α expression is increased in a variety of tumors but this is not restricted to hypoxic regions. We have previously shown that cyclin-dependent kinase 1 (CDK1) stabilizes HIF1α through direct phosphorylation of its Ser668 residue in a Von Hippel-Lindau (VHL)-independent manner both under hypoxia and at G2/M under normoxia (Warfel et al., Cell Cycle, 2013, 12, 3689-701). Another previously acknowledged VHL-independent HIF1α stabilizer is the heat shock protein 90 (HSP90) (Isaacs et al., J. Biol. Chem., 2002, 277, 29936-44) that has been correlated with adverse prognosis and recognized as a therapeutic target in cancer (Calderwood et al., Trends Biochem. Sci., 2016, 41, 311-323). We investigated herein crosstalk between CDK1-mediated and HSP90-mediated HIF1α stabilization and the involvement of therapeutic targeting.

SUMMARY

The present disclosure provides pharmaceutical compositions comprising: a cyclin-dependent kinase inhibitor (CDKI) and a heat shock protein 90 (HSP90) inhibitor, wherein the pharmaceutical composition does not comprise a combination of RO-3306 and geldanamycin.

In some embodiments, the inhibitor of CDK is Kenpaullone, PKC-412, Butyrolactone I, Cdk1/5 Inhibitor, Flavopiridol (Alvocidib) (such as, Flavopiridol hydrochloride), N9-Isopropyl-olomoucine, Indirubin-3'-monoxime, NU2058, Olomoucine II, 9-Cyanopaullone, 5-Iodo-Indirubin-3'-monoxime, NU6102, Oxindole I, SU 9516, Roscovitine, RO-3306, 10Z-Hymenialdisine, AZD 5438, AT7519, Dinaciclib, R547, CGP 74514A, SNS-032 (BMS-387032), BMS-265246, JNJ-7706621, PHA-793887, P276-00, PHA-767491, Milciclib (PHA-848125), NU6027, LDC000067, ribociclib (Kisqali®), palbociclib (Ibrance®), or abemaciclib (Vernenio®). In some embodiments, the inhibitor of CDK is Roscovitine, palbociclib, or abemaciclib. In some embodiments, the inhibitor of CDK is Roscovitine. In some embodiments, the inhibitor of CDK is palbociclib. In some embodiments, the inhibitor of CDK is abemaciclib.

In some embodiments, the inhibitor of HSP90 is 17-AAG (Tanespimycin), Luminespib (AUY-922, NVP-AUY922), 17-DMAG, (Alvespimycin) HCl, Ganetespib (STA-9090), Apoptozole, BIIB021, Onalespib (AT13387), NVP-BEP800, geldanamycin, SNX-2112 (PF-04928473), PF-04929113 (SNX-5422), KW-2478, XL888, NMS-E973, PU-H71, DEB10-0932, DS-2248, MPC-3100, TAS-116, Radicicol, gamitrinib, Elesclomol (STA-4783), TRC051384, KRIBB11, BIIB021, KNK437, VER-49009, CH5138303, VER-50589, VER155008, or HSP990 (NVP-HSP990). In some embodiments, the inhibitor of HSP90 is Ganetespib (STA-9090) or Onalespib (AT13387). In some embodiments, the inhibitor of HSP90 is Ganetespib (STA-9090). In some embodiments, the inhibitor of HSP90 is Onalespib (AT13387).

In some embodiments, the inhibitor of CDK is Roscovitine and the inhibitor of HSP90 is Ganetespib (STA-9090). In some embodiments, the inhibitor of CDK is palbociclib and the inhibitor of HSP90 is Ganetespib (STA-9090). In some embodiments, the inhibitor of CDK is palbociclib and the inhibitor of HSP90 is Onalespib (AT13387). In some embodiments, the inhibitor of CDK is abemaciclib and the inhibitor of HSP90 is Ganetespib (STA-9090). In some embodiments, the inhibitor of CDK is abemaciclib and the inhibitor of HSP90 is Onalespib (AT13387).

The present disclosure also provides methods of treating cancer or a tumor in a subject in need thereof, comprising: administering a CDK inhibitor to the subject; and administering an HSP90 inhibitor to the subject; provided that both RO-3306 and geldanamycin are not administered to the subject.

In some embodiments, the inhibitor of CDK is Kenpaullone, PKC-412, Butyrolactone I, Cdk1/5 Inhibitor, Flavopiridol (Alvocidib) (such as, Flavopiridol hydrochloride), N9-Isopropyl-olomoucine, Indirubin-3'-monoxime, NU2058, Olomoucine II, 9-Cyanopaullone, 5-Iodo-Indirubin-3'-monoxime, NU6102, Oxindole I, SU 9516, Roscovitine, RO-3306, 10Z-Hymenialdisine, AZD 5438, AT7519, Dinaciclib, R547, CGP 74514A, SNS-032 (BMS-387032), BMS-265246, JNJ-7706621, PHA-793887, P276-00, PHA-767491, Milciclib (PHA-848125), NU6027, LDC000067, ribociclib (Kisqali®), palbociclib (Ibrance®), or abemaciclib (Vernenio®). In some embodiments, the inhibitor of CDK is Roscovitine, palbociclib, or abemaciclib. In some embodiments, the inhibitor of CDK is Roscovitine. In some embodiments, the inhibitor of CDK is palbociclib. In some embodiments, the inhibitor of CDK is abemaciclib.

In some embodiments, the inhibitor of HSP90 is 17-AAG (Tanespimycin), Luminespib (AUY-922, NVP-AUY922), 17-DMAG, (Alvespimycin) HCl, Ganetespib (STA-9090), Apoptozole, BIIB021, Onalespib (AT13387), NVP-BEP800, geldanamycin, SNX-2112 (PF-04928473), PF-04929113 (SNX-5422), KW-2478, XL888, NMS-E973, PU-H71, DEB10-0932, DS-2248, MPC-3100, TAS-116, Radicicol, or gamitrinib. In some embodiments, the inhibitor of HSP90 is Ganetespib (STA-9090).

In some embodiments, the inhibitor of CDK is Roscovitine and the inhibitor of HSP90 is Ganetespib (STA-9090). In some embodiments, the inhibitor of CDK is palbociclib and the inhibitor of HSP90 is Ganetespib (STA-9090). In some embodiments, the inhibitor of CDK is palbociclib and the inhibitor of HSP90 is Onalespib (AT13387). In some embodiments, the inhibitor of CDK is abemaciclib and the inhibitor of HSP90 is Ganetespib (STA-9090). In some embodiments, the inhibitor of CDK is abemaciclib and the inhibitor of HSP90 is Onalespib (AT13387).

In some embodiments, the CDK inhibitor and the HSP90 inhibitor are both present in a single pharmaceutical composition.

In some embodiments, the cancer is lung cancer, breast cancer, colon cancer, renal cancer, glioblastoma, or colorectal cancer.

DESCRIPTION OF EMBODIMENTS

Figure 1:
FIG. 1 shows CDK1 inhibition disrupts the interaction between HSP90 and HIF1α in HCT116 colon cancer cells under hypoxia; the interaction was detected by co-immunoprecipitation with exogenously introduced HA-HIF1α.
Figure 1:
Figure 1:
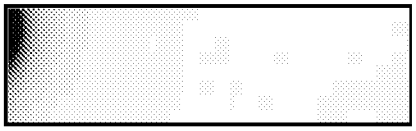

As shown herein, under hypoxia, the interaction between HSP90 and HIF1α proteins is impaired by CDK1 inhibition in HCT116 colon cancer cells. HIF1α level is decreased by HSP90 inhibition under hypoxia, which can be further reduced by the combination of HSP90 inhibition and CDK1 knockdown. Combinational inhibition of CDK1 and HSP90 synergistically suppresses HCT116 proliferation under both normoxia and hypoxia. The joint inhibitory effect of CDK1 and HSP90 on HIF1α level is observed in other colorectal cancer cell lines as well.

Unless defined otherwise, all technical and scientific terms have the same meaning as is commonly understood by one of ordinary skill in the art to which the disclosed embodiments belong.

As used herein, the terms "a" or "an" mean "at least one" or "one or more" unless the context clearly indicates otherwise.

As used herein, the term "about" means that the recited numerical value is approximate and small variations would not significantly affect the practice of the disclosed embodiments. Where a numerical value is used, unless indicated otherwise by the context, "about" means the numerical value can vary by ±10% and remain within the scope of the disclosed embodiments.

As used herein, the term "animal" includes, but is not limited to, mammals, humans and non-human vertebrates, such as wild, domestic, and farm animals.

As used herein, the terms "antagonize" and "antagonizing" mean reducing or completely eliminating one or more effects.

As used herein, the term "carrier" means a diluent, adjuvant, or excipient with which a compound is administered in a composition.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive and open-ended and include the options following the terms, and do not exclude additional, unrecited elements or method steps.

As used herein, the term "contacting" means bringing together two compounds, molecules, or entities in an in vitro system or an in vivo system.

As used herein, the terms "individual," "subject," and "patient," used interchangeably, mean any animal described herein.

As used herein, the phrase "in need thereof" means that the "individual," "subject," or "patient" has been identified as having a need for the particular method, prevention, or treatment. In some embodiments, the identification can be by any means of diagnosis. In any of the methods, preventions, and treatments described herein, the "individual," "subject," or "patient" can be in need thereof. In some embodiments, the "individual," "subject," or "patient" is in an environment or will be traveling to an environment, or has traveled to an environment in which a particular disease, disorder, or condition is prevalent.

As used herein, the term "isolated" means that the compounds, or pharmaceutically acceptable salts thereof, described herein are separated from other components of either: a) a natural source, such as a plant or cell, such as a bacterial culture, or b) a synthetic organic chemical reaction mixture, such as by conventional techniques.

As used herein, the term "mammal" means a rodent (i.e., a mouse, a rat, or a guinea pig), a monkey, a sheep, a cat, a dog, a cow, a horse, a pig, or a human. In some embodiments, the mammal is a human.

As used herein, the phrase "pharmaceutically acceptable" means that the compounds, materials, compositions, and/or dosage forms are within the scope of sound medical judgment and are suitable for use in contact with tissues of humans and other animals. In some embodiments, "pharmaceutically acceptable" means approved by a regulatory agency of the Federal government or a state government or listed in the U.S. Pharmacopeia or other generally recognized pharmacopeia for use in animals, and more particularly in humans. In some embodiments, the pharmaceutically acceptable compounds, materials, compositions, and/or dosage forms result in no persistent detrimental effect on the subject, or on the general health of the subject being treated. However, it will be recognized that transient effects, such as minor irritation or a "stinging" sensation, are common with administration of medicament and the existence of such transient effects is not inconsistent with the composition, formulation, or ingredient (e.g., excipient) in question.

As used herein, the terms "prevention" or "preventing" mean a reduction of the risk of acquiring a particular disease, condition, or disorder.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor, or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be based on, for example, the age, health, size, and sex of the subject. Optimal amounts can also be determined based on monitoring of the subject's response to treatment.

As used herein, the terms "treat," "treated," or "treating" mean both therapeutic treatment and prophylactic or preventative measures wherein the object is to prevent or slow down (lessen) an undesired physiological condition, disorder or disease, or obtain beneficial or desired clinical results. For purposes herein, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response, optionally without excessive levels of side effects. Treatment also includes prolonging survival as compared to expected survival if not receiving treatment.

It should be appreciated that particular features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

The present disclosure provides pharmaceutical compositions comprising at least one cyclin-dependent kinase inhibitor (CDKI), and a least one heat shock protein 90 (HSP90) inhibitor, wherein the pharmaceutical composition does not comprise a combination of RO-3306 and geldanamycin. In some embodiments, the inhibitor of CDK is Kenpaullone, PKC-412, Butyrolactone I, Cdk1/5 Inhibitor, Flavopiridol (Alvocidib) (such as, Flavopiridol hydrochloride), N9-Isopropyl-olomoucine, Indirubin-3'-monoxime, NU2058, Olomoucine II, 9-Cyanopaullone, 5-Iodo-Indirubin-3'-monoxime, NU6102, Oxindole I, SU 9516, Roscovitine, RO-3306, 10Z-Hymenialdisine, AZD 5438, AT7519, Dinaciclib, R547, CGP 74514A, SNS-032 (BMS-387032), BMS-265246, JNJ-7706621, PHA-793887, P276-00, PHA-767491, Milciclib (PHA-848125), NU6027, LDC000067, ribociclib (Kisqali®), palbociclib (Ibrance®), or abemaciclib (Vernenio®). In some embodiments, the inhibitor of CDK is Roscovitine, palbociclib, or abemaciclib. In some embodiments, the inhibitor of CDK is Roscovitine. In some embodiments, the inhibitor of CDK is palbociclib. In some embodiments, the inhibitor of CDK is abemaciclib. In some embodiments, the inhibitor of HSP90 is 17-AAG (Tanespimycin), Luminespib (AUY-922, NVP-AUY922), 17-DMAG, (Alvespimycin) HCl, Ganetespib (STA-9090), Apoptozole, BIIB021, Onalespib (AT13387), NVP-BEP800, geldanamycin, SNX-2112 (PF-04928473), PF-04929113 (SNX-5422), KW-2478, XL888, NMS-E973, PU-H71, DEB10-0932, DS-2248, MPC-3100, TAS-116, Radicicol, or gamitrinib. In some embodiments, the inhibitor of HSP90 is Ganetespib or Onalespib. In some embodiments, the inhibitor of HSP90 is Ganetespib. In some embodiments, the inhibitor of HSP90 is Onalespib. In some embodiments, the inhibitor of CDK is Roscovitine and the inhibitor of HSP90 is Ganetespib (STA-9090). In some embodiments, the inhibitor of CDK is palbociclib and the inhibitor of HSP90 is Ganetespib (STA-9090). In some embodiments, the inhibitor of CDK is palbociclib and the inhibitor of HSP90 is Onalespib (AT13387). In some embodiments, the inhibitor of CDK is abemaciclib and the inhibitor of HSP90 is Ganetespib (STA-9090). In some embodiments, the inhibitor of CDK is abemaciclib and the inhibitor of HSP90 is Onalespib (AT13387).

Suitable compositions include, but are not limited to, oral non-absorbed compositions. Suitable compositions also include, but are not limited to saline, water, cyclodextrin solutions, and buffered solutions of pH 3-9.

The compounds described herein, or pharmaceutically acceptable salts thereof, can be formulated with numerous excipients including, but not limited to, purified water, propylene glycol, PEG 400, glycerin, DMA, ethanol, benzyl alcohol, citric acid/sodium citrate (pH3), citric acid/sodium citrate (pH5), tris(hydroxymethyl)amino methane HCl (pH7.0), 0.9% saline, and 1.2% saline, and any combination thereof. In some embodiments, excipient is chosen from propylene glycol, purified water, and glycerin.

In some embodiments, the excipient is a multi-component system chosen from 20% w/v propylene glycol in saline, 30% w/v propylene glycol in saline, 40% w/v propylene glycol in saline, 50% w/v propylene glycol in saline, 15% w/v propylene glycol in purified water, 30% w/v propylene glycol in purified water, 50% w/v propylene glycol in purified water, 30% w/v propylene glycol and 5 w/v ethanol in purified water, 15% w/v glycerin in purified water, 30% w/v glycerin in purified water, 50% w/v glycerin in purified water, 20% w/v Kleptose in purified water, 40% w/v Kleptose in purified water, and 25% w/v Captisol in purified water. In some embodiments, the excipient is chosen from 50% w/v propylene glycol in purified water, 15% w/v glycerin in purified water, 20% w/v Kleptose in purified water, 40% w/v Kleptose in purified water, and 25% w/v Captisol in purified water. In some embodiments, the excipient is chosen from 20% w/v Kleptose in purified water, 20% w/v propylene glycol in purified water, and 15% w/v glycerin in purified water.

In some embodiments, the composition comprises 50 mg/mL of compound in 20% w/v Kleptose in purified water.

In some embodiments, the formulation can be lyophilized to a solid and reconstituted with, for example, water prior to use.

When administered to a mammal (e.g., to an animal for veterinary use or to a human for clinical use) the compounds can be administered in isolated form.

When administered to a human, the compounds can be sterile. Water is a suitable carrier when the compound of Formula I is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions described herein can take the form of a solution, suspension, emulsion, tablet, pill, pellet, capsule, capsule containing a liquid, powder, sustained-release formulation, suppository, aerosol, spray, or any other form suitable for use. Examples of suitable pharmaceutical carriers are described in Remington's Pharmaceutical Sciences, A. R. Gennaro (Editor) Mack Publishing Co.

In one embodiment, the compounds are formulated in accordance with routine procedures as a pharmaceutical composition adapted for administration to humans. Typically, compounds are solutions in sterile isotonic aqueous buffer. Where necessary, the compositions can also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound is to be administered by infusion, it can be dispensed, for example, with an infusion bottle containing sterile pharmaceutical grade water or saline. Where the compound is administered by injection, an ampoule of sterile water for injection or saline can be provided so that the ingredients may be mixed prior to administration.

The pharmaceutical compositions can be in unit dosage form. In such form, the composition can be divided into unit doses containing appropriate quantities of the active component. The unit dosage form can be a packaged preparation, the package containing discrete quantities of the preparations, for example, packeted tablets, capsules, and powders in vials or ampules. The unit dosage form can also be a capsule, cachet, or tablet itself, or it can be the appropriate number of any of these packaged forms.

In some embodiments, a composition of the present disclosure is in the form of a liquid wherein the active agent is present in solution, in suspension, as an emulsion, or as a solution/suspension. In some embodiments, the liquid composition is in the form of a gel. In other embodiments, the liquid composition is aqueous. In other embodiments, the composition is in the form of an ointment.

Suitable compositions, formulations, and excipients are those that cause no substantial detrimental effect, even of a transient nature.

Acceptable excipients include, but are not limited to, viscosity-enhancing agents, preservatives, stabilizers, antioxidants, suspending agents, solubilizing agents, buffering agents, lubricating agents, or salts, and combinations thereof.

For example, some compositions, when in suspension or solution form, are suitably viscous or mucoadhesive, or both viscous or mucoadhesive, and thus comprise a viscosity-enhancing agent. Examples of suitable viscosity-enhancing agents include, but are not limited to, glycerin, polyvinyl alcohol, polyvinyl pyrrolidone, methylcellulose, hydroxypropylmethylcellulose, hydroxyethyl-cellulose, carboxymethylcellulose, hydroxypropylcellulose, and/or various gelling agents. For example, in some embodiments, the viscosity-enhancing agent is chosen from methylcellulose, hydroxypropylmethyl-cellulose, polyvinyl alcohol, and glycerol. Such agents are generally employed in the compositions at a concentration of about 0.01% to about 3% by weight.

In some embodiments, the excipient is a viscosity-enhancing agent or a promoter of mucoadhesion, such as carboxymethylcellulose. In such embodiments, the concentration of carboxymethylcellulose in the aqueous suspension or solution is 0.1% to 5% by weight or about 0.1% to about 2.5% by weight. The carboxymethylcellulose is preferably in the form of sodium carboxymethylcellulose substituted to a degree that the sodium content of the sodium carboxymethylcellulose is about 1% to about 20%.

Suitable preservatives include, but are not limited to, mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; and sorbic acid and salts thereof.

Optionally one or more stabilizers can be included in the compositions to enhance chemical stability where required. Suitable stabilizers include, but are not limited to, chelating agents or complexing agents, such as, for example, the calcium complexing agent ethylene diamine tetraacetic acid (EDTA). For example, an appropriate amount of EDTA or a salt thereof, e.g., the disodium salt, can be included in the composition to complex excess calcium ions and prevent gel formation during storage. EDTA or a salt thereof can suitably be included in an amount of about 0.01% to about 0.5%. In those embodiments containing a preservative other than EDTA, the EDTA or a salt thereof, more particularly disodium EDTA, can be present in an amount of about 0.025% to about 0.1% by weight.

One or more antioxidants can also be included in the compositions. Suitable antioxidants include, but are not limited to, ascorbic acid, sodium metabisulfite, sodium bisulfite, acetylcysteine, polyquaternium-1, benzalkonium chloride, thimerosal, chlorobutanol, methyl paraben, propyl paraben, phenylethyl alcohol, edetate disodium, sorbic acid, or other agents know to those of skill in the art. Such preservatives are typically employed at a level of from about 0.001% to about 1.0% by weight.

In some embodiments, the compounds are solubilized at least in part by an solubilizing agent. Certain nonionic surfactants, for example polysorbate 80, can be useful as solubilizing agents, as can glycols, polyglycols, e.g., polyethylene glycol 400 (PEG-400), and glycol ethers.

Suitable solubilizing agents for solution and solution/suspension compositions are cyclodextrins. Suitable cyclodextrins can be chosen from α-cyclodextrin, β-cyclodextrin, γ-cyclodextrin, alkylcyclodextrins (e.g., methyl-β-cyclodextrin, dimethyl-β-cyclodextrin, diethyl-β-cyclodextrin), hydroxyalkylcyclodextrins (e.g., hydroxyethyl-β-cyclodextrin, hydroxypropyl-β-cyclodextrin), carboxy-alkylcyclodextrins (e.g., carboxymethyl-β-cyclodextrin), sulfoalkylether cyclodextrins (e.g., sulfobutylether-β-cyclodextrin), and the like.

A cyclodextrin can optionally be present in a composition at a concentration from about 1 to about 200 mg/ml, from about 5 to about 100 mg/ml, or from about 10 to about 50 mg/ml.

One or more pH adjusting agents and/or buffering agents can be included in the compositions, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

One or more acceptable salts can be included in the compositions in an amount required to bring osmolality of the composition into an acceptable range. Such salts include, but are not limited to, those having sodium, potassium or ammonium cations and chloride, citrate, ascorbate, borate, phosphate, bicarbonate, sulfate, thiosulfate or bisulfite anions. In some embodiments, salts include sodium chloride, potassium chloride, sodium thiosulfate, sodium bisulfite and ammonium sulfate. In some embodiments, the salt is sodium chloride.

Optionally one or more surfactants, preferably nonionic surfactants, or co-solvents can be included in the compositions to enhance solubility of the components of the compositions or to impart physical stability, or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40; polysorbate 20, 60 and 80; polyoxyethylene/polyoxypropylene surfactants (e.g., Pluronic® F-68, F84 and P-103); cyclodextrin; or other agents known to those of skill in the art. Typically, such co-solvents or surfactants are employed in the compositions at a level of from about 0.01% to about 2% by weight.

Compositions typically include a combination of one or more of the optional excipients listed above. For example, in some embodiments, the composition can optionally further comprise glycerin in an amount from about 0.5% to about 5%, from about 1% to about 2.5%, or from about 1.5% to about 2% by weight. Glycerin can be useful to increase viscosity of the composition and for adjustment of osmolality. Independently of the presence of glycerin, the composition can also further comprise a cyclodextrin, such as hydroxypropyl-β-cyclodextrin, in an amount from about 0.5% to about 25% by weight, as a solubilizing agent, and an antimicrobially effective amount of a preservative, e.g., imidazolidinyl urea in an amount from about 0.03% to about 0.5%; methylparaben in an amount from about 0.015% to about 0.25%; propylparaben in an amount from about 0.005% to about 0.01%; phenoxyethanol in an amount from about 0.25% to about 1%; disodium EDTA in an amount from about 0.05% to about 0.2%; thimerosal in an amount from 0.001% to about 0.15%; chlorobutanol in an amount from about 0.1% to about 0.5%; and/or sorbic acid in an amount from about 0.05% to about 0.2%; all by weight.

The compositions can be prepared by methods known in the art and described in patents and publications cited herein and incorporated herein by reference.

The present disclosure also provides pharmaceutical packs or kits comprising one or more containers filled with one or more compounds or compositions described herein. Optionally associated with such container(s) can be a notice in the form prescribed by a governmental agency regulating the manufacture, use or sale of pharmaceuticals or biological products, which notice reflects approval by the agency of manufacture, use or sale for human administration for treating a condition, disease, or disorder described herein. In some embodiments, the kit contains more than one compound described herein. In some embodiments, the kit comprises a compound described herein in a single injectable dosage form, such as a single dose within an injectable device such as a syringe with a needle. In some embodiments, the dosage form may be a strip pack or a blister pack.

The present disclosure also provides methods of treating cancer or a tumor in a subject in need thereof, comprising: administering a CDK inhibitor to the subject, and administering an HSP90 inhibitor to the subject, provided that both RO-3306 and geldanamycin are not administered to the subject. In some embodiments, the CDK inhibitor and the HSP90 inhibitor are both present in a single pharmaceutical composition. In some embodiments, the cancer is lung cancer, breast cancer, colon cancer, renal cancer, glioblastoma, or colorectal cancer.

In some embodiments, the inhibitor of CDK is Kenpaullone, PKC-412, Butyrolactone I, Cdk1/5 Inhibitor, Flavopiridol (Alvocidib) (such as, Flavopiridol hydrochloride), N9-Isopropyl-olomoucine, Indirubin-3'-monoxime, NU2058, Olomoucine II, 9-Cyanopaullone, 5-Iodo-Indirubin-3'-monoxime, NU6102, Oxindole I, SU 9516, Roscovitine, RO-3306, 10Z-Hymenialdisine, AZD 5438, AT7519, Dinaciclib, R547, CGP 74514A, SNS-032 (BMS-387032), BMS-265246, JNJ-7706621, PHA-793887, P276-00, PHA-767491, Milciclib (PHA-848125), NU6027, LDC000067, ribociclib (Kisqali®), palbociclib (Ibrance®), or abemaciclib (Vernenio®). In some embodiments, the inhibitor of CDK is Roscovitine, palbociclib, or abemaciclib. In some embodiments, the inhibitor of CDK is Roscovitine. In some embodiments, the inhibitor of CDK is palbociclib. In some embodiments, the inhibitor of CDK is abemaciclib. In some embodiments, the inhibitor of HSP90 is 17-AAG (Tanespimycin), Luminespib (AUY-922, NVP-AUY922), 17-DMAG, (Alvespimycin) HCl, Ganetespib (STA-9090), Apoptozole, BIIB021, Onalespib (AT13387), NVP-BEP800, geldanamycin, SNX-2112 (PF-04928473), PF-04929113 (SNX-5422), KW-2478, XL888, NMS-E973, PU-H71, DEB10-0932, DS-2248, MPC-3100, TAS-116, Radicicol, or gamitrinib. In some embodiments, the inhibitor of HSP90 is Ganetespib or Onalespib. In some embodiments, the inhibitor of HSP90 is Ganetespib. In some embodiments, the inhibitor of HSP90 is Onalespib. In some embodiments, the inhibitor of CDK is Roscovitine and the inhibitor of HSP90 is Ganetespib (STA-9090). In some embodiments, the inhibitor of CDK is palbociclib and the inhibitor of HSP90 is Ganetespib (STA-9090). In some embodiments, the inhibitor of CDK is palbociclib and the inhibitor of HSP90 is Onalespib (AT13387). In some embodiments, the inhibitor of CDK is abemaciclib and the inhibitor of HSP90 is Ganetespib (STA-9090). In some embodiments, the inhibitor of CDK is abemaciclib and the inhibitor of HSP90 is Onalespib (AT13387).

Generally, cancer refers to any malignant growth or tumor caused by abnormal and uncontrolled cell division; it may spread to other parts of the body through the lymphatic system or the blood stream. Cancers include both solid tumors and blood-borne tumors. Cancers that are treatable are broadly divided into the categories of carcinoma, lymphoma and sarcoma. Examples of carcinomas include, but are not limited to: adenocarcinoma, acinic cell adenocarcinoma, adrenal cortical carcinomas, alveoli cell carcinoma, anaplastic carcinoma, basaloid carcinoma, basal cell carcinoma, bronchiolar carcinoma, bronchogenic carcinoma, renaladinol carcinoma, embryonal carcinoma, anometroid carcinoma, fibrolamolar liver cell carcinoma, follicular carcinomas, giant cell carcinomas, hepatocellular carcinoma, intraepidermal carcinoma, intraepithelial carcinoma, leptomanigio carcinoma, medullary carcinoma, melanotic carcinoma, menigual carcinoma, mesometonephric carcinoma, oat cell carcinoma, squamal cell carcinoma, sweat gland carcinoma, transitional cell carcinoma, and tubular cell carcinoma. Sarcomas include, but are not limited to: amelioblastic sarcoma, angiolithic sarcoma, botryoid sarcoma, endometrial stroma sarcoma, ewing sarcoma, fascicular sarcoma, giant cell sarcoma, granulositic sarcoma, immunoblastic sarcoma, juxaccordial osteogenic sarcoma, coppices sarcoma, leukocytic sarcoma (leukemia), lymphatic sarcoma (lympho sarcoma), medullary sarcoma, myeloid sarcoma (granulocitic sarcoma), austiogenci sarcoma, periosteal sarcoma, reticulum cell sarcoma (histiocytic lymphoma), round cell sarcoma, spindle cell sarcoma, synovial sarcoma, and telangiectatic audiogenic sarcoma. Lymphomas include, but are not limited to: Hodgkin's disease and lymphocytic lymphomas, such as Burkitt's lymphoma, NPDL, NML, NH and diffuse lymphomas.

Thus, examples of cancers that can be treated using the compounds described herein include, but are not limited to, Hodgkin's disease, non-Hodgkin's lymphomas, acute lymphocytic leukemia, multiple myeloma, breast carcinomas, ovarian carcinomas, lung carcinomas, Wilms' tumor, testicular carcinomas, soft-tissue sarcomas, chronic lymphocytic leukemia, primary macroglobulinemia, bladder carcinomas, chronic granulocytic leukemia, primary brain carcinomas, malignant melanoma, small-cell lung carcinomas, stomach carcinomas, colon carcinomas, malignant pancreatic insulinoma, malignant carcinoid carcinomas, malignant melanomas, choriocarcinomas, mycosis fungoides, head and neck carcinomas, osteogenic sarcoma, pancreatic carcinomas, acute granulocytic leukemia, hairy cell leukemia, rhabdomyosarcoma, Kaposi's sarcoma, genitourinary carcinomas, thyroid carcinomas, esophageal carcinomas, malignant hypercalcemia, renal cell carcinomas, endometrial carcinomas, polycythemia vera, essential thrombocytosis, adrenal cortex carcinomas, skin cancer, and prostatic carcinomas.

In some embodiments, the cancer is lung cancer (such as non-small cell lung cancer), breast cancer, prostate cancer, ovarian cancer, testicular cancer, colon cancer, renal cancer, bladder cancer, pancreatic cancer, glioblastoma, neuroblastoma, sarcomas such as Kaposi's sarcoma and Ewing's sarcoma, hemangiomas, solid tumors, blood-borne tumors, rhabdomyosarcoma, CNS cancer (such as brain cancer), retinoblastoma, neuroblastoma, leukemia, melanoma, kidney or renal cancer, and osteosarcoma. In some embodiments, the cancer is lung cancer, breast cancer, colon cancer, renal cancer, glioblastoma, or colorectal cancer. In some embodiments, the cancer is colon cancer or colorectal cancer. In some embodiments, the cancer is a metastatic cancer.

The compounds can be used in methods of killing or inhibiting the growth of cancer cells, either in vivo or in vitro, or inhibiting the growth of a cancerous tumor.

The compounds and compositions described herein can be administered by any route of administration including, but not limited to, oral, sublingual, buccal, rectal, intranasal, inhalation, eye drops, ear drops, epidural, intracerebral, intracerebroventricular, intrathecal, epicutaneous or transdermal, subcutaneous, intradermal, intravenous, intraarterial, intraosseous infusion, intramuscular, intracardiac, intraperitoneal, intravesical infusion, and intravitreal. In some embodiments, the administration is oral, sublingual, buccal, rectal, intranasal, inhalation, eye drops, or ear drops. In some embodiments, the administration is oral, sublingual, buccal, rectal, intranasal, or inhalation. In some embodiments, the administration is epidural, intracerebral, intracerebroventricular, or intrathecal. In some embodiments, the administration is epicutaneous or transdermal, subcutaneous, or intradermal. In some embodiments, the administration is intravenous, intraarterial, intraosseous infusion, intramuscular, intracardiac, intraperitoneal, intravesical infusion, or intravitreal. In some embodiments, the administration is intravenous, intramuscular, or intraperitoneal. The route of administration can depend on the particular disease, disorder, or condition being treated and can be selected or adjusted by the clinician according to methods known to the clinician to obtain desired clinical responses. Methods for administration are known in the art and one skilled in the art can refer to various pharmacologic references for guidance (see, for example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980)).

In some embodiments, it may be desirable to administer one or more compounds, or a pharmaceutically acceptable salt thereof, to a particular area in need of treatment. This may be achieved, for example, by local infusion (for example, during surgery), topical application (for example, with a wound dressing after surgery), by injection (for example, by depot injection), catheterization, by suppository, or by an implant (for example, where the implant is of a porous, non-porous, or gelatinous material, including membranes, such as sialastic membranes, or fibers). Formulations for injection can be presented in unit dosage form, such as in ampoules or in multi-dose containers, with an added preservative.

The compounds described herein can be formulated for parenteral administration by injection, such as by bolus injection or continuous infusion. The compounds can be administered by continuous infusion subcutaneously over a period of about 15 minutes to about 24 hours. The compositions can take such forms as suspensions, solutions or emulsions in oily or aqueous vehicles, and can contain formulatory agents such as suspending, stabilizing and/or dispersing agents. In some embodiments, the injectable is in the form of short-acting, depot, or implant and pellet forms injected subcutaneously or intramuscularly. In some embodiments, the parenteral dosage form is the form of a solution, suspension, emulsion, or dry powder.

For oral administration, the compounds described herein can be formulated by combining the compounds with pharmaceutically acceptable carriers well known in the art. Such carriers enable the compounds to be formulated as tablets, pills, dragees, capsules, emulsions, liquids, gels, syrups, caches, pellets, powders, granules, slurries, lozenges, aqueous or oily suspensions, and the like, for oral ingestion by a patient to be treated. Pharmaceutical preparations for oral use can be obtained by, for example, adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations including, but not limited to, maize starch, wheat starch, rice starch, potato starch, gelatin, gum tragacanth, methyl cellulose, hydroxypropylmethylcellulose, sodium carboxymethylcellulose, and polyvinylpyrrolidone (PVP). If desired, disintegrating agents can be added, including, but not limited to, the cross-linked polyvinyl pyrrolidone, agar, or alginic acid or a salt thereof such as sodium alginate.

Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, when in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds. Oral compositions can include standard vehicles such as, for example, mannitol, lactose, starch, magnesium stearate, sodium saccharine, cellulose, magnesium carbonate, etc. Such vehicles are suitably of pharmaceutical grade.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added.

For buccal administration, the compounds and compositions can take the form of, such as, tablets or lozenges formulated in a conventional manner.

For administration by inhalation, the compounds and compositions described herein can be delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, such as gelatin for use in an inhaler or insufflator can be formulated containing a powder mix of the compound and a suitable powder base such as lactose or starch.

The compounds and compositions described herein can also be formulated in rectal compositions such as suppositories or retention enemas, such as containing conventional suppository bases such as cocoa butter or other glycerides. The compounds described herein can also be formulated in vaginal compositions such as vaginal creams, suppositories, pessaries, vaginal rings, and intrauterine devices.

In transdermal administration, the compounds and compositions can be applied to a plaster, or can be applied by transdermal, therapeutic systems that are consequently supplied to the organism. In some embodiments, the compounds are present in creams, solutions, powders, fluid emulsions, fluid suspensions, semi-solids, ointments, pastes, gels, jellies, and foams, or in patches containing any of the same.

The compounds and compositions described herein can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In yet another embodiment, the compounds and compositions can be delivered in a controlled release system. In one embodiment, a pump may be used (see Langer, supra; Sefton, CRC Crit. Ref. Biomed. Eng., 1987, 14, 201; Buchwald et al., Surgery, 1980, 88, 507 Saudek et al., N. Engl. J. Med., 1989, 321, 574). In some embodiments, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger et al., J. Macromol. Sci. Rev. Macromol. Chem., 1983, 23, 61; see, also Levy et al., Science, 1985, 228, 190; During et al., Ann. Neurol., 1989, 25, 351; Howard et al., J. Neurosurg., 1989, 71, 105). In some embodiments, a controlled-release system can be placed in proximity of the target of the compounds described herein, such as the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, Science, 1990, 249, 1527-1533) may be used.

The compounds and compositions described herein can be contained in formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The pharmaceutical compositions can also comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols. In some embodiments, the compounds described herein can be used with agents including, but not limited to, topical analgesics (e.g., lidocaine), barrier devices (e.g., GelClair), or rinses (e.g., Caphosol). Pharmaceutical carriers can be liquids, such as water and oils, including those of petroleum, animal, vegetable or synthetic origin, such as peanut oil, soybean oil, mineral oil, sesame oil, and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used.

In some embodiments, the compounds and compositions described herein can be delivered in a vesicle, in particular a liposome (see, Langer, Science, 1990, 249, 1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

The compounds and compositions described herein can be administered either alone (as a single compound or one or more compounds described herein) or in combination (concurrently or serially) with other pharmaceutical agents. For example, the compounds and compositions can be administered in combination with any one or more of the following:

1) anti-cancer or anti-neoplastic agents (for example, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel) or therapies (for example, surgery or radiotherapy);

2) antibiotics (for example: a) protein synthesis inhibitors including, but not limited to, amikacin, anisomycin, apramycin, azithromycin, blasticidine S, brefeldin A, butirosin, chloramphenicol, chlortetracycline, clindamycin, clotrimazole, cycloheximide, demeclocycline, dibekacin, dihydrostreptomycin, doxycycline, duramycin, emetine, erythromycin, fusidic acid, G 418, gentamicin, helvolic acid, hygromycin B, josamycin, kanamycin, kirromycin, lincomycin, meclocycline, mepartricin, midecamycin, minocycline, neomycin, netilmicin, nitrofurantoin, nourseothricin, oleandomycin, oxytetracycline, paromomycin, puromycin, rapamycin, ribostamycin, rifampicin, rifamycin, rosamicin, sisomicin, spectinomycin, spiramycin, streptomycin, tetracycline, domeclocycline, thiamphenicol, methacycline, thiostrepton, tobramycin, tunicamycin, tylosin, viomycin, and virginiamycin; b) DNA synthesis interfering agents including, but not limited to, camptothecin, 10-deacetylbaccatin III, azacytidine, 7-aminoactinomycin D, 8-quinolinol, 9-dihydro-13-acetylbaccatin III, aclarubicin, actinomycin D, actinomycin I, actinomycin V, bafilomycin A1, bleomycin, capreomycin, chromomycin, cinoxacin, ciprofloxacin, norfloxacin, cis-diammineplatinum(II) dichloride, coumermycin A1, L(+)-lactic acid, cytochalasin B, cytochalasin D, dacarbazine, daunorubicin, distamycin A, doxorubicin, echinomycin, enrofloxacin, etoposide, flumequine, formycin, fumagillin, ganciclovir, gliotoxin, lomefloxacin, metronidazole, mithramycin A, mitomycin C, nalidixic acid, netropsin, nitrofurantoin, nogalamycin, nonactin, novobiocin, ofloxacin, oxolinic acid, paclitaxel, phenazine, phleomycin, pipemidic acid, rebeccamycin, sinefungin, streptonigrin, streptozocin, succinylsulfathiazole, sulfadiazine, sulfadimethoxine, sulfaguanidine purum, sulfamethazine, sulfamonomethoxine, sulfanilamide, sulfaquinoxaline, sulfasalazine, sulfacetamide, sulfathiazole, trimethoprim, tubercidin, 5-azacytidine, cordycepin, and formycin A; c) cell wall synthesis interfering agents including, but not limited to, (+)-6-aminopenicillanic acid, 7-Aminodesacetoxycephalosporanic acid, amoxicillin, ampicillin, azlocillin, bacitracin, carbenicillin, cefaclor, cefamandole, cefazolin, cefmetazole, cefixime, cefoperazone, cefotaxime, cefsulodin, ceftriaxone, cephalexin, cephalosporin C, cephalothin, cephradine, ceftazidime, cloxacillin, D-cycloserine, dicloxacillin, D-penicillamine, ceftizoxime, econazole, ethambutol, lysostaphin, moxalactam, nafcillin, nikkomycin Z, nitrofurantoin, oxacillin, penicillic, penicillin G, phenethicillin, phenoxymethylpenicillinic acid, phosphomycin, pipemidic acid, piperacillin, ristomycin, and vancomycin; d) cell membrane permeability interfering agents (ionophores) including, but not limited to, amphotericin B, 2-mercaptopyridine, 4-bromocalcimycin A23187, colistin, alamethicin, calcimycin A23187, chlorhexidine, clotrimazole, econazole, hydrocortisone, filipin, gliotoxin, gramicidin A, gramicidin C, ionomycin, lasalocid A, lonomycin A, monensin, narasin, nigericin, nisin, N-(6-aminohexyl)-5-chloro-1-naphthalenesulfonamide, sulfisoxazole, pyrimethamine, mafenide, nonactin, nystatin, phenazine, pimaricin, polymyxin B, DL-penicillamine, praziquantel, salinomycin, surfactin, and valinomycin; e) enzyme inhibitors including, but not limited to, (+)-usnic acid, (±)-miconazole, (S)-(+)-camptothecin, 1-deoxymannojirimycin, 2-heptyl-4-hydroxyquinoline N-oxide, cordycepin, antimycin, 1,10-phenanthroline, 6-diazo-5-oxo-L-norleucine, 8-quinolinol, antipain, ascomycin, azaserine, bafilomycin, cerulenin, chloroquine, cinoxacin, ciprofloxacin, mevastatin, concanamycin A, concanamycin C, coumermycin A1, L(+)-lactic acid, cyclosporin A, econazole, enrofloxacin, etoposide, flumequine, formycin A, furazolidone, fusaric acid, geldanamycin, gliotoxin, gramicidin A, gramicidin C, herbimycin A, indomethacin, irgasan, lomefloxacin, mycophenolic acid, myxothiazol, nalidixic acid, netropsin, niclosamide, N-(6-aminohexyl)-5-chloro-1-naphthalenesulfonamide, N-methyl-1-deoxynojirimycin, nikkomycin, nogalamycin, nonactin, novobiocin, ofloxacin, oleandomycin, oligomycin, oxolinic acid, piericidin A, pipemidic acid, radicicol, rapamycin, rebeccamycin, sinefungin, staurosporine, stigmatellin, succinylsulfathiazole, succinylsulfathiazole, sulfadiazine, sulfadimethoxine, sulfaguanidine, sulfamethazine, sulfamonomethoxine, sulfanilamide, sulfaquinoxaline, sulfasalazine, sulfathiazole, triacsin C, trimethoprim, and vineomycin A1; f) membrane modifiers including, but not limited to, paracelsin); g) aminoglycosides; and h) fluoroquinolones;

3) statins (for example, atorvastatin, pravastatin, fluvastatin, lovastatin, simvastatin, and cerivastatin);

4) PPAR agonists (for example, troglitazone, pioglitazone, rosiglitazone, ciglitazone, 5-((4-(2-(methyl-2-pyridinylamino)ethoxy)phenyl)methyl)-2,4-thiazolidinedione, AD 5075, WAY-120,744, englitazone, darglitazone, gemfibrozil, fenofibrate, clofibrate, and ciprofibrate);

5) bile-acid-binding resin (for example, e cholestyramine and colestipol hydrochloride);

6) RXR agonists (for example, LG 100268, LGD 1069, 9-cis retinoic acid, 2-(1-(3,5,5,8,8-pentamethyl-5,6,7,8-tetrahydro-2-naphthyl)-cyclopropyl)-pyridine-5-carboxylic acid, and 4-((3,5,5,8,8-pentamethyl-5,6,7,8-tetrahydro-2-naphthyl)2-carbonyl)-benzoic acid);

7) anti-obesity agents (for example, β-3 receptor agonists, sibutramine, bupropion, fluoxetine, and phentermine);

8) hormones (for example, thyroid hormone, estrogen, and insulin);

9) insulin secretagog (for example, forskolin, dibutryl cAMP, and isobutylmethylxanthine);

10) tyrophostines (for example, tryophostine 51);

11) sulfonylurea-based agents (for example, glisoxepid, glyburide, acetohexamide, chlorpropamide, glibornuride, tolbutamide, tolazamide, glipizide, gliclazide, gliquidone, glyhexamide, phenbutamide, and tolcyclamide);

12) biguanides (for example, metformin, phenformin, and buformin);

13) α-glucosidase inhibitors (for example, acarbose and miglitol);

14) apo A-I agonists (for example, the Milano form of apo A-I (apo A-IM));

15) cardiovascular agents (for example, methyldopa, diazoxide, hydralazine, phentolamine, amrinone, milrinone, enoximone, fenoximone, imazodan, sulmazole, ranitine, bosentan, and rezulin);

16) anti-inflammatory agents (for example, steroidal anti-inflammatory agents, non-steroidal anti-inflammatory agents (NSAIDs), and selective cyclooxygenase-2 inhibitors);

17) topical and/or regional anesthetic agents;

18) anti-allergic agents (for example, anti-histamines);

19) demulcents or mucoprotective agents (for example, pectin, glycerin, honey, syrup, and herbs such as, for example, coltsfoot (*Tussilago farfara*), comfrey (*Symphytum officinale*), common purslane (*Portulaca oleracea*), corn silk (*Zea mays*), couchgrass (*Agropyrum repens*), dead nettle (*Lamium*), flaxseed (*Linum usitatissimum*), irish moss (*Chondrus crispus*), lungwort (*Sticta pulmonaria*), liquorice (*Glycyrrhiza glabra*), loquat (*Eriobotrya japonica*), mallow (*Malva sylvestris*), marshmallow (*Althaea officinalis*), mullein (*Verbascum thapsus*), oatmeal (*Avena sativa*), parsley piert (*Aphanes arvensis*), plantain (*Plantago major*), and slippery elm (*Ulmus rubra*);

20) acetylcholine blocking agents;

21) adrenergic agonists;

22) beta-adrenergic blocking agents; and 23) anti-hypertensives.

The amount of compounds and compositions to be administered may be that amount which is therapeutically effective. The dosage to be administered may depend on the characteristics of the subject being treated, e.g., the particular animal treated, age, weight, health, types of concurrent treatment, if any, and frequency of treatments, and on the nature and extent of the disease, condition, or disorder, and can be easily determined by one skilled in the art (e.g., by the clinician). The selection of the specific dose regimen can be selected or adjusted or titrated by the clinician according to methods known to the clinician to obtain the desired clinical response. In addition, in vitro or in vivo assays may optionally be employed to help identify optimal dosage ranges. The precise dose to be employed in the compositions may also depend on the route of administration, and should be decided according to the judgment of the practitioner and each patient's circumstances.

Suitable dosage ranges for oral administration include, but are not limited to, from about 0.001 mg/kg body weight to about 200 mg/kg body weight, from about 0.01 mg/kg body weight to about 100 mg/kg body weight, from about 0.01 mg/kg body weight to about 70 mg/kg body weight, from about 0.1 mg/kg body weight to about 50 mg/kg body weight, from 0.5 mg/kg body weight to about 20 mg/kg body weight, or from about 1 mg/kg body weight to about 10 mg/kg body weight. In some embodiments, the oral dose is about 5 mg/kg body weight.

Suitable dosage ranges for intravenous administration include, but are not limited to, from about 0.01 mg/kg body weight to about 500 mg/kg body weight, from about 0.1 mg/kg body weight to about 100 mg/kg body weight, from about 1 mg/kg body weight to about 50 mg/kg body weight, or from about 10 mg/kg body weight to about 35 mg/kg body weight.

Suitable dosage ranges for other routes of administration can be calculated based on the forgoing dosages as known by one skilled in the art. For example, recommended dosages for intradermal, intramuscular, intraperitoneal, subcutaneous, epidural, sublingual, intracerebral, transdermal, or inhalation are in the range from about 0.001 mg/kg body weight to about 200 mg/kg body weight, from about 0.01 mg/kg body weight to about 100 mg/kg body weight, from about 0.1 mg/kg body weight to about 50 mg/kg body weight, or from about 1 mg/kg body weight to about 20 mg/kg body weight. Effective doses may be extrapolated from dose-response curves derived from in vitro or animal model test systems. Such animal models and systems are well known in the art.

In some embodiments, a CDK inhibitor is administered concurrently (in or not in the same pharmaceutical composition) or serially with the administration of an HSP90 inhibitor. In some embodiments, the CDK inhibitor is administered prior to the HSP90 inhibitor or subsequent to the HSP90 inhibitor. In some embodiments, combination therapy involves alternating between administering a CDK inhibitor and an HSP90 inhibitor. The duration of administration of each drug or therapeutic agent can be, e.g., one month, three months, six months, or a year.

The present disclosure also provides one or more compounds described above, or a pharmaceutically acceptable salt thereof, or a pharmaceutical composition comprising one or more compounds described above, for treating a cancer or tumor.

The present disclosure also provides one or more compounds described above, or a pharmaceutically acceptable salt thereof, or a pharmaceutical composition comprising one or more compounds described above, for use in the manufacture of a medicament for the treatment of a cancer or a tumor.

The present disclosure also provides the use of one or more compounds described above, or a pharmaceutically acceptable salt thereof, or a pharmaceutical composition comprising one or more compounds described above, for treating cancer or a tumor.

The present disclosure also provides the use of one or more compounds described above, or a pharmaceutically acceptable salt thereof, or a pharmaceutical composition comprising one or more compounds described above, for treating cancer or a tumor.

In order that the subject matter disclosed herein may be more efficiently understood, examples are provided below. It should be understood that these examples are for illustrative purposes only and are not to be construed as limiting the claimed subject matter in any manner.

EXAMPLES

Example 1: Materials and Methods

Cell Culture

HCT116, SW480, HT29, DLD1, and RKO cells were obtained from American Type Culture Collection. HCT116 and HT29 cells were maintained in McCoy's 5A medium (Hyclone) with 10% fetal bovine serum (FBS, Hyclone) and 1% penicillin/streptomycin (P/S). SW480, DLD1, and RCC4 cells were maintained in Dulbecco's modified Eagle medium (Hyclone) with 10% FBS and 1% P/S. RKO cells were maintained in RPMI 1640 medium (Hyclone) with 10% FBS and 1% P/S. Cells were regularly tested and authenticated. All cell lines were maintained at 37° C. in 5% $CO_2$. As for hypoxia treatment, cells were kept in a hypoxia chamber (In vivo[2], Ruskinn) which maintains 0.5% $O_2$.

Antibodies and Reagents

HIF1α and Ran antibodies was purchased from BD Biosciences. CDK1 and CDK4 antibodies were purchased from Santa Cruz Biotechnology. HA, PARP and clvd PARP antibodies was purchased from Cell Signaling Technology. Actin antibody was purchased from Sigma. MG-132 was purchased from Sigma. Ro-3306 was purchased from Santa Cruz Biotechnology. PD-0332991 (palbociclib) was purchased from Medkoo Biosciences. Geldanamycin was purchased from Invivogen. Ganetespib was purchased from ApexBio or Medkoo Biosciences.

Western Blot

Treated cells were lysed in RIPA buffer (Sigma). Protein concentrations were determined using a BCA Protein Assay Kit (Life Technologies). Equal amounts of total protein were boiled with LDS sample buffer (Thermo Fisher Scientific) and reducing agent (Invitrogen). Samples were analyzed with SDS-PAGE. Proteins were transferred to an Immobilon-P PVDF membrane (EMD Millipore). First and secondary antibodies were added in order. Signals were detected after addition of the ECL western blotting substrate (Thermo Fisher Scientific).

Cell Transfection

Transient transfection of DNA was performed using Opti-MEM (Thermo Fisher Scientific) and Lipofectamine 2000 (Life Technologies), pcDNA3-HA-HIF1α plasmid was purchased from Addgene. Knockdown experiments were performed with Opti-MEM and Lipofectamine RNAiMAX (Life Technologies), according to the manufacturer's protocol. Control, CDK1 and CDK4 siRNAs were purchased from Santa Cruz Biotechnology.

Immunoprecipitation

HCT116 cells were transiently transfected with pcDNA3-HA-HIF1α. After 24 hours, cells were treated in hypoxia for 6 hours with MG132 (1 μM). Cells were washed with PBS and fixed in 4% formaldehyde. Lysis was performed in RIPA buffer with gentle sonication. Protein concentration in the lysates was measured and equalized. Part of the lysate was analyzed by SDS-PAGE and western blot for input monitoring. The remaining majority was incubated with anti-HA antibody overnight at 4° C., followed by precipitation with Protein A/G Ultra link Resin for about 2 to 4 hours.

Synergy Analysis

Indicated cells were seeded in a 96-well black microplate (Greiner Bio-One) and treated with combinations of reagents at various concentrations for 48 or 72 hours in normoxia or hypoxia. CellTiter-Glo reagent (Promega) was added and mixed on an orbital shaker at room temperature. Luminescence was recorded as a readout to compare cell number difference. Combination index between two treatments was calculated using Compusyn software. Synergism was indicated by index value<1.

Sub-G1 Analysis

HCT116 cells were treated with indicated reagents for 48 or 72 hours in normoxia or hypoxia. Culture media including floating cells were collected and combined with trypsinized (Gemini Bio-Products) attached cells. All harvested cells were washed in PBS with 1% FBS. Cells were fixed with cold 70% ethanol at 4° C. Subsequently, cells were washed, incubated in phosphate citrate buffer, and stained with propidium iodide (Sigma). Percentage of sub-G1 population was analyzed by flow cytometry.

Migration Assay

The indicated cell lines were plated in 12-well plates at 80-90% confluence. Scratch lines were made with a 200-μL pipette tip. After washed with PBS, cells were cultured in media containing reagents as indicated. Images were captured at both the beginning and end of the experiment. Gap width was measured in each image. Each treatment group contains three replicates.

Example 2: Studies

Animal experiments were in compliance with the Institutional Animal Care and Use Committee and obeyed Guide for the Care and Use of Laboratory Animals. Hairless combined immunodeficient (SCID) mice were monitored in Laboratory Animal Facility at Fox Chase Cancer Center. HT29 cells were subcutaneously injected into the flanks of 4-week old mice on both sides at $1 \times 10^6/100$ μL in Matrigel/PBS. Treatments were started when tumors reached about 100 to 125 $mm^3$ as measured by vernier caliper. Tumor-bearing mice were treated with palbociclib or ganetespib or the combination of both. Palbociclib was administered orally via gavage at 50 mg/kg daily (dissolved in $ddH_2O$). Ganetespib was administered intravaneously via retro-orbital injection at 25 mg/kg weekly (dissolved in 10% DMSO, 18% Cremophor RH 40, 3.8% dextrose). At the endpoint, mice were euthanized, and tumors were dissected. The fixation, embedding (with Paraffin), sectioning and hematoxylin and eosin (H&E) staining of tumor samples were performed by Histopathology Facility at Fox Chase Cancer Center. Results are presented as the mean±standard deviation (SD). Difference comparisons were performed with Prism software using the Student's two-tailed t test. Statistically significant difference was determined by P value<0.05.

CDK1 inhibition disrupts the interaction between HSP90 and HIF1α in HCT116 colon cancer cells under hypoxia (see, FIG. 1). The interaction was detected by co-immunoprecipitation with exogenously introduced HA-HIF1α.

Figure 2:
FIG. 2 shows heat shock upregulates HIF1α in normoxia, which is reversed by the treatment with HSP90 inhibitor geldanamycin or CDK1 inhibitor Ro-3306 in HCT116.

Heat shock upregulates HIF1α in normoxia, which is reversed by the treatment with HSP90 inhibitor geldanamycin or CDK1 inhibitor Ro-3306 in HCT116 (see, FIG. 2).

Figure 3:
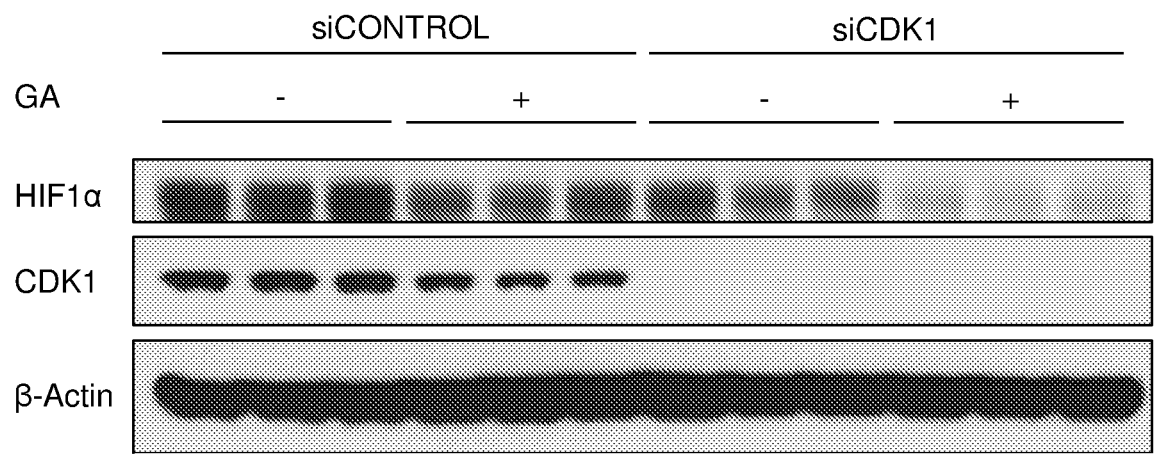
FIG. 3 shows the protein level of HIF1α is robustly reduced by the combination of CDK1 knockdown and HSP90 inhibition under hypoxia in HCT116.

The protein level of HIF1α is robustly reduced by the combination of CDK1 knockdown and HSP90 inhibition under hypoxia in HCT116 (see, FIG. 3).

Figure 4:
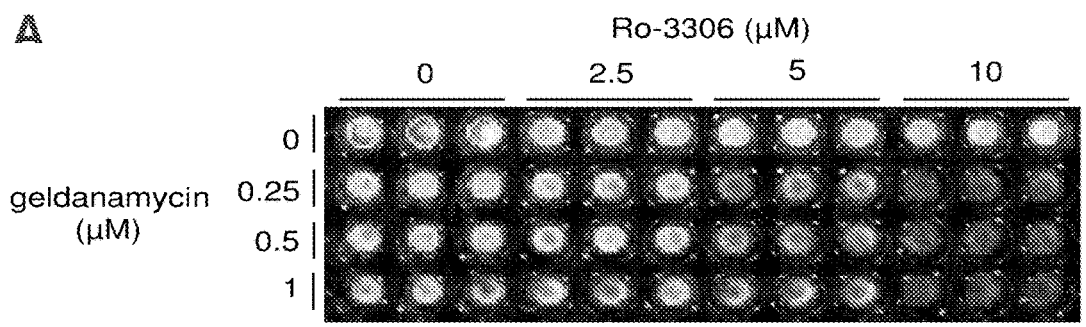
FIG. 4 (Panels A and B) show synergistic inhibition of cell proliferation by CDK1 and HSP90 inhibitors; HCT116 cells were treated with indicated combinations (Panel A) for 48 hours in normoxia (21% $O_2$) or (Panel 4) for 72 hours in hypoxia (0.5% $O_2$).
Figure 4:
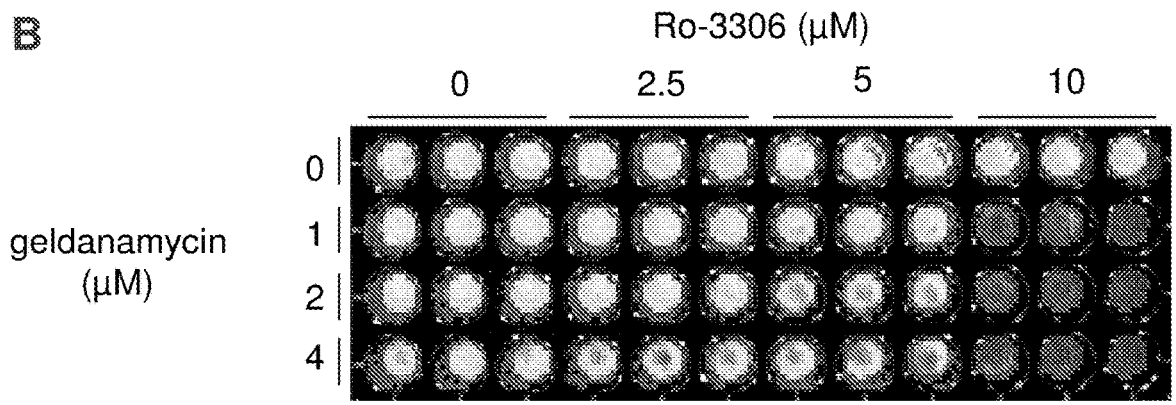

The inhibition of cell proliferation by CDK1 and HSP90 inhibitors is synergistic (see, FIG. 4, Panels A and B). HCT116 cells were treated with indicated combinations (Panel A) for 48 hours in normoxia (21% $O_2$) or (Panel 4) for 72 hours in hypoxia (0.5% $O_2$).

Figure 5:
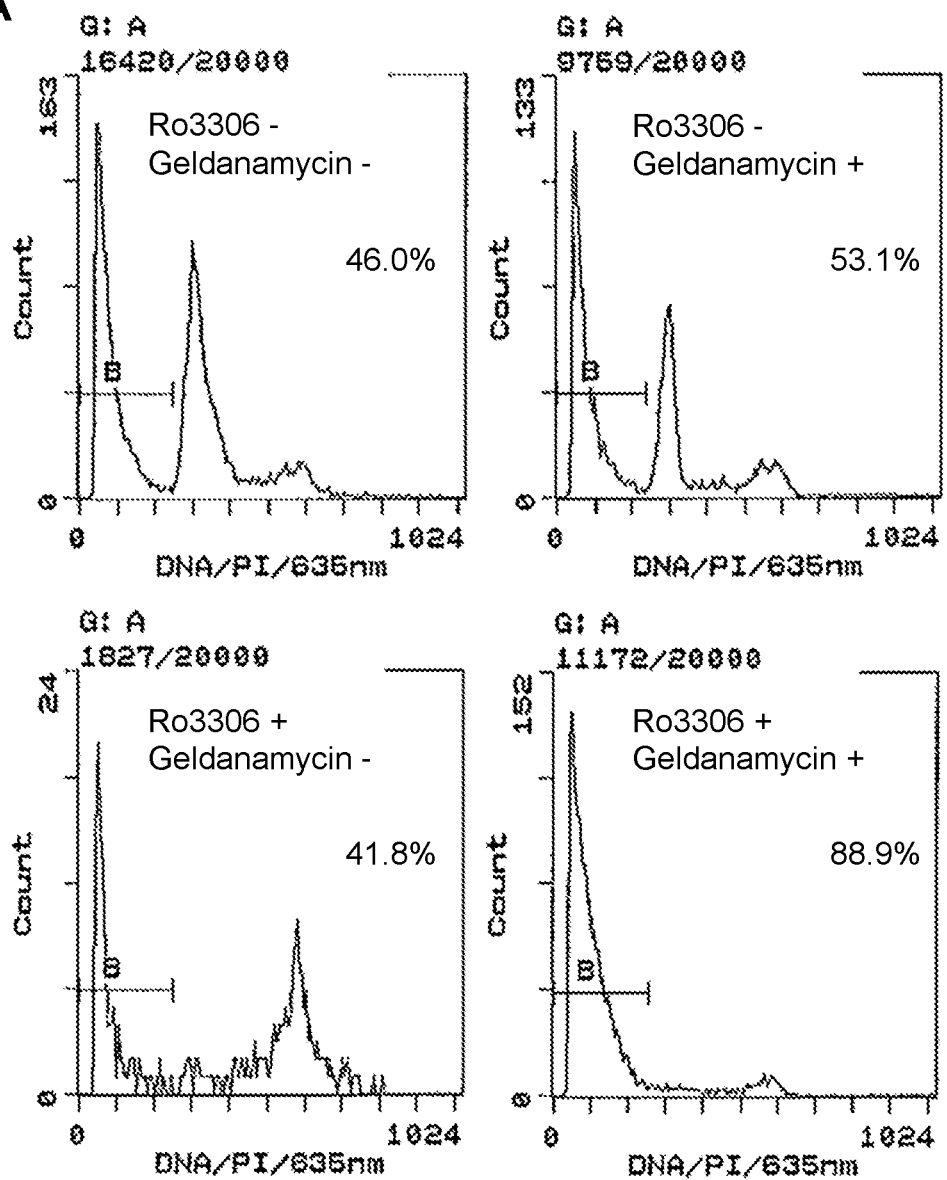
FIG. 5 (Panels A and B) show sub-G1 measurement of HCT116 treated for 72 hours under hypoxia; (Panel A) representatives and (Panel B) quantification of flow cytometry results.
Figure 5:
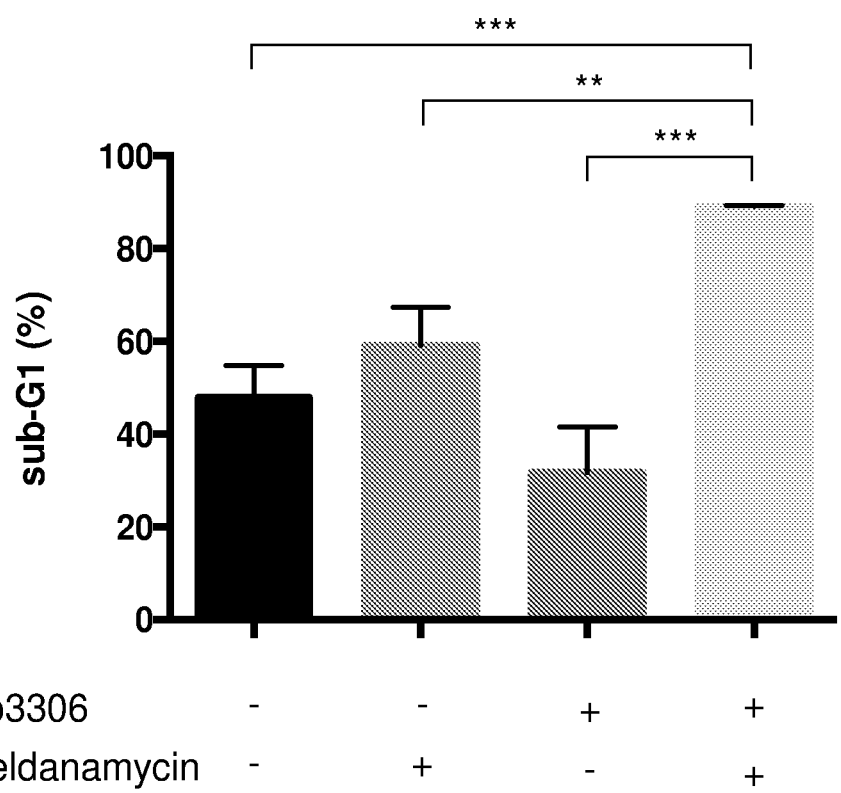

Sub-G1 of HCT116 treated for 72 hours under hypoxia was measured (see, FIG. 5, Panels A and B). Panel A shows representatives and Panel B shows quantification of flow cytometry results.

Figure 6:
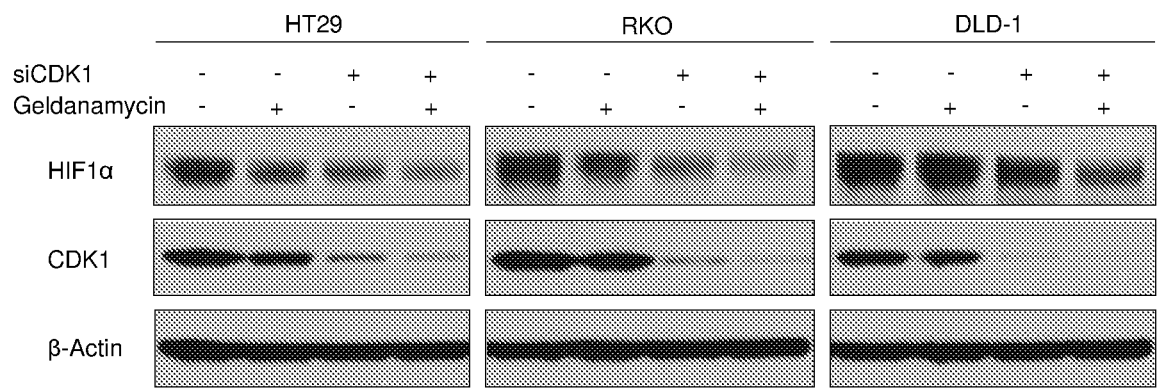
FIG. 6 shows CDK1 deficiency enhances HSP90 inhibition-induced HIF1α inhibition in other colorectal cell lines (HT29, RKO, and DLD1).

CDK1 deficiency enhances HSP90 inhibition-induced HIF1α inhibition in other colorectal cell lines (HT29, RKO, and DLD1) (see, FIG. 6).

Figure 7:
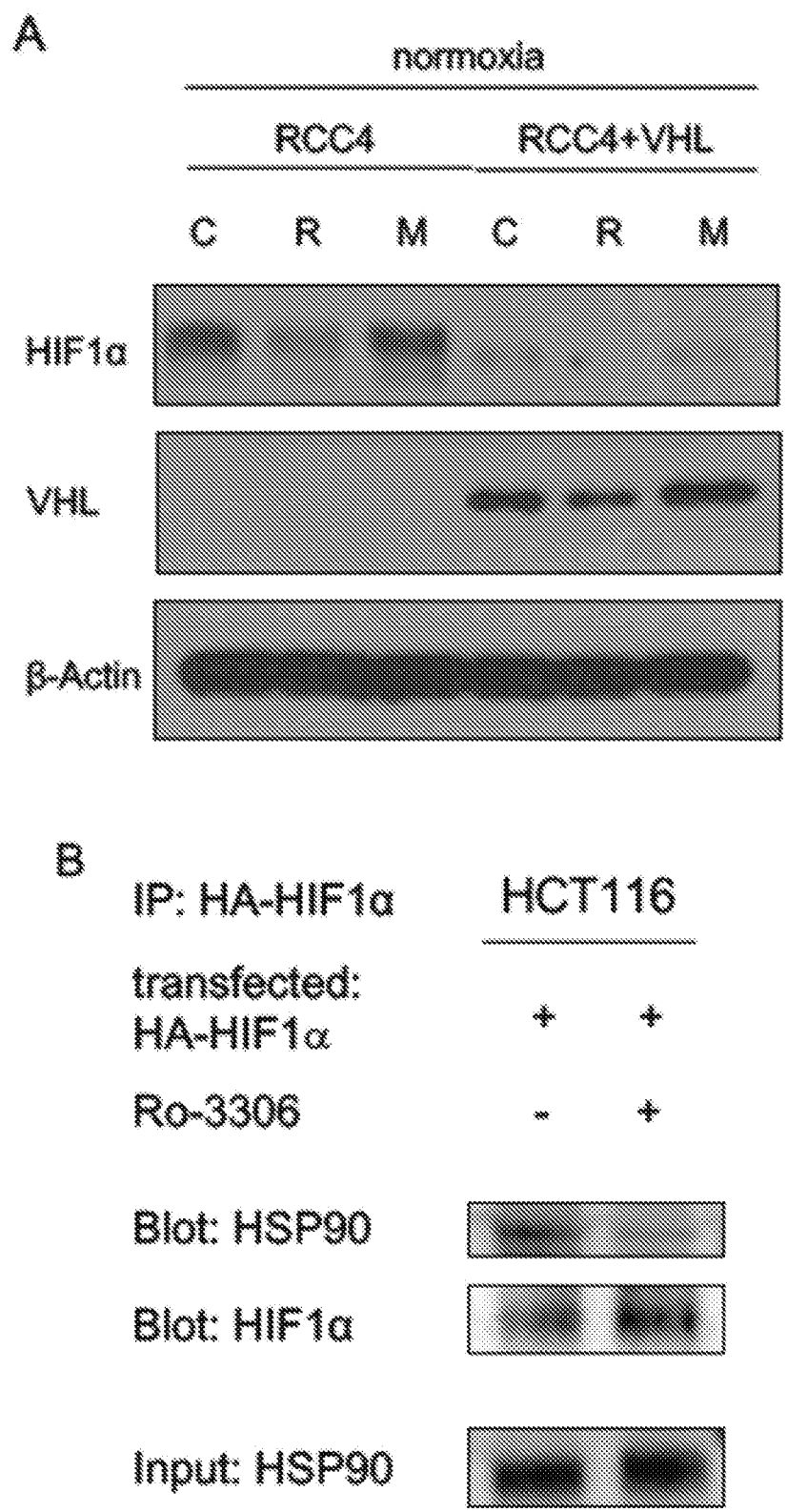
FIG. 7 (Panels A, B, and C) shows CDK1 contribution to HSP90-mediated HIF1α stabilization; (Panel A) inhibition of CDK1 (for 6 hours under normoxia) decreases the level of HIF1α in RCC4 cells independently of VHL presence; C: control, R: Ro-3306, M: MG132; (Panel B) CDK1 inhibition (for 6 hours under hypoxia) impairs the interaction between HIF1α and HSP90; and (Panel C) CDK1 partially reversed heat shock (at 40° C.)-induced HIF1α expression.
Figure 7:
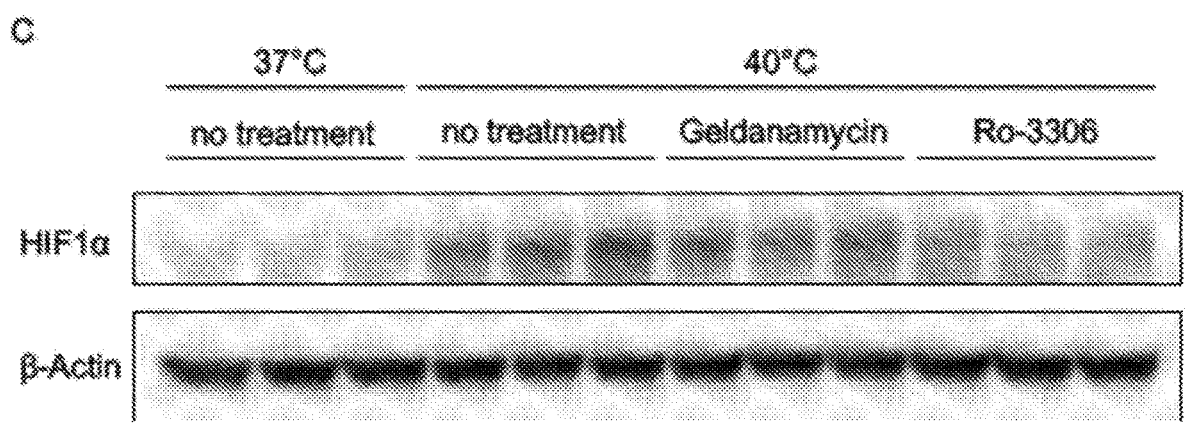

CDK1 contributed to HSP90-mediated HIF1α stabilization (see, FIG. 7, Panels A, B, and C). Panel A shows that inhibition of CDK1 (for 6 hours under normoxia) decreases the level of HIF1α in RCC4 cells independently of VHL presence (C: control, R: Ro-3306, M: MG132). Panel B shows that CDK1 inhibition (for 6 hours under hypoxia) impairs the interaction between HIF1α and HSP90. Panel C shows that CDK1 partially reversed heat shock (at 40° C.)-induced HIF1α expression.

Figure 8:
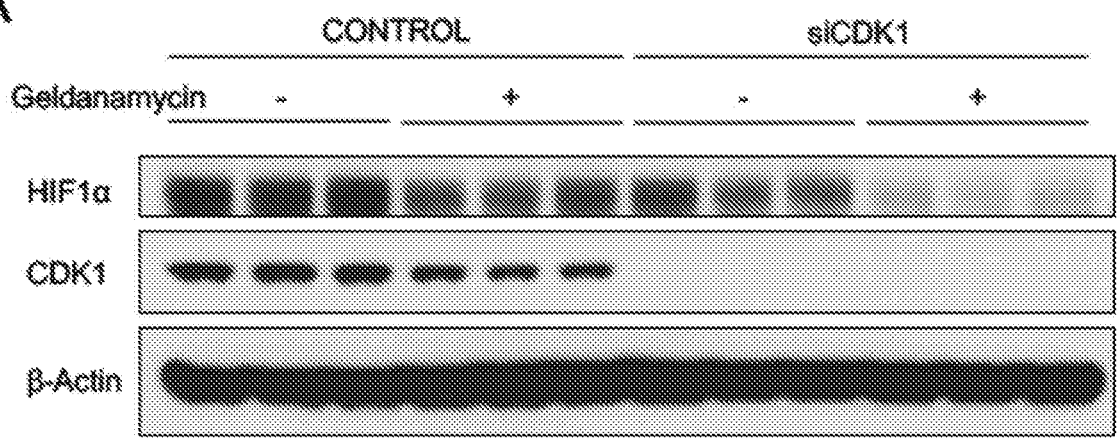
FIG. 8 (Panels A, B, C, and D) show dual inhibition of CDK1 and HSP90 robustly reduces the level of HIF1α; (Panel A) HCT116, (Panel C) HCT116p53$^{-/-}$ cells or (Panel D) other colorectal cell lines were treated with control or CDK1 siRNA for 48 hours, followed by treatment with DMSO or geldanamycin in hypoxia for 6 hours; (Panel B) cells were treated with Ro-3306, geldanamycin, or the combination of both for 6 hours under hypoxia.
Figure 8:
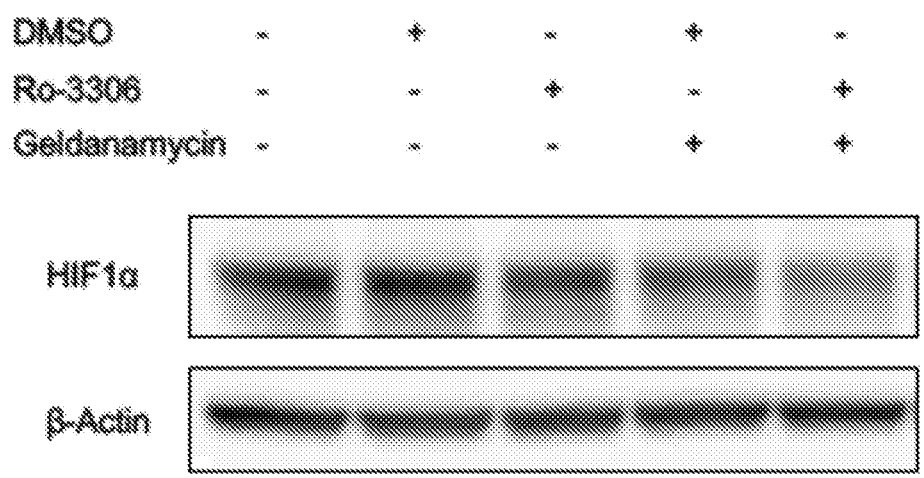
Figure 8:
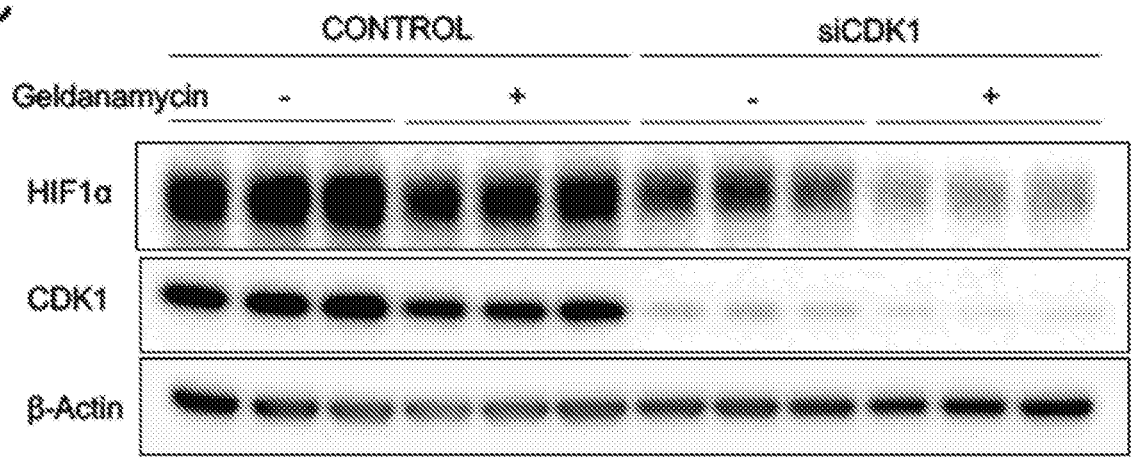
Figure 8:
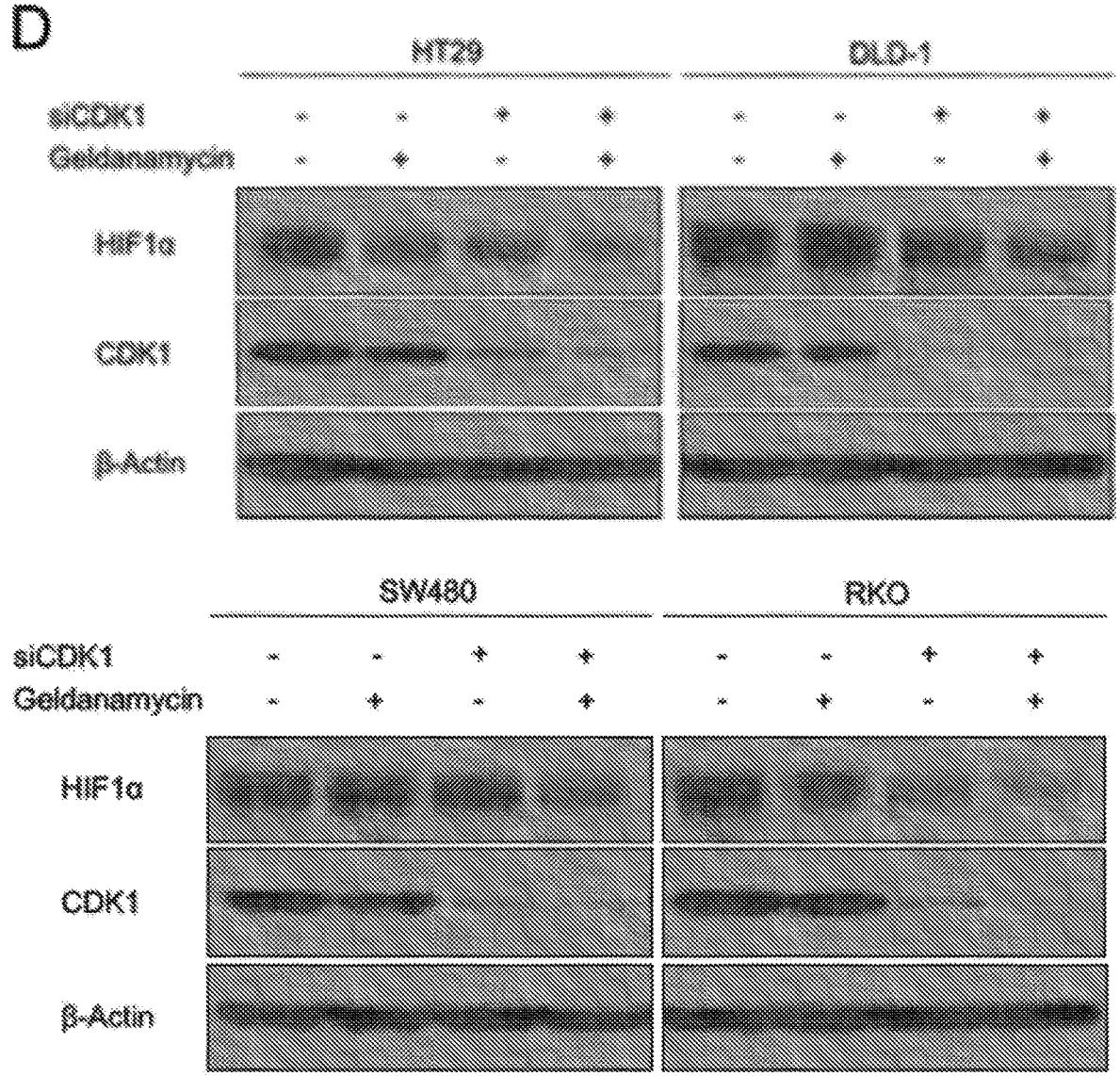

Dual inhibition of CDK1 and HSP90 robustly reduces the level of HIF1α (see, FIG. 8, Panels A, B, C, and D). HCT116 (see, Panel A), HCT116p53$^{-/-}$ cells (see, Panel C) or other colorectal cell lines (see, Panel D) were treated with control or CDK1 siRNA for 48 hours, followed by treatment with DMSO or geldanamycin in hypoxia for 6 hours. Cells were treated with Ro-3306, geldanamycin, or the combination of both for 6 hours under hypoxia (see, Panel B).

Figure 9:
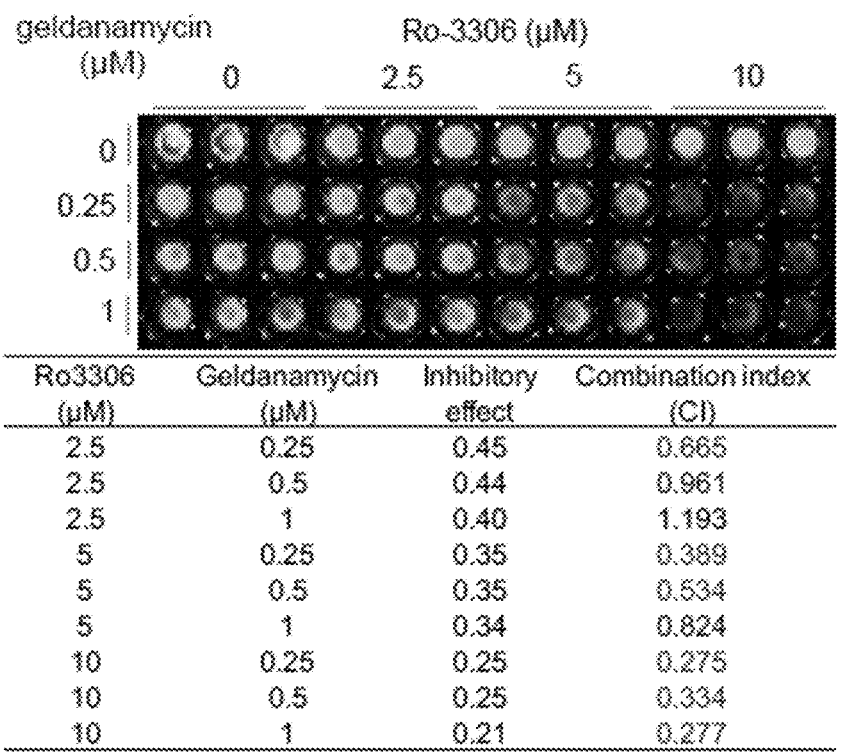
FIG. 9 (Panels A, B, C, D, and E) show Ro-3306 and geldanamycin synergistically inhibit HCT116 cell viability through induction of apoptosis; (Panel A) in normoxia or (Panel B) hypoxia, cells were treated with Ro-3306 and geldanamycin at indicated concentrations for (Panel A) 48 hours or (Panel B) 72 hours; (Panel C) sub-G1 analysis by flow cytometry of cells treated with Ro-3306 at 10 μM and geldanamycin at 1 μM under normoxia for 48 hours or under hypoxia for 72 hours; (Panel D) Western blot of PARP cleavage in cells treated with Ro-3306 or geldanamycin or both; (Panel E) CellTiter-Glo analysis of cell viability in HCT116Bax$^{-/-}$ cells treated at indicated concentrations under normoxia for 48 hours.
Figure 9:
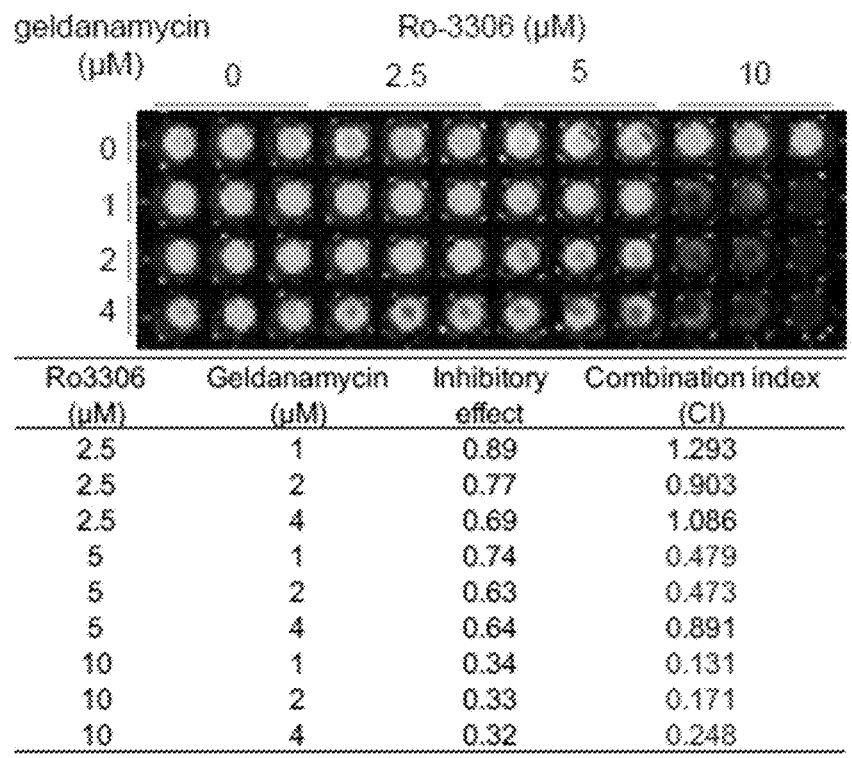
Figure 9:
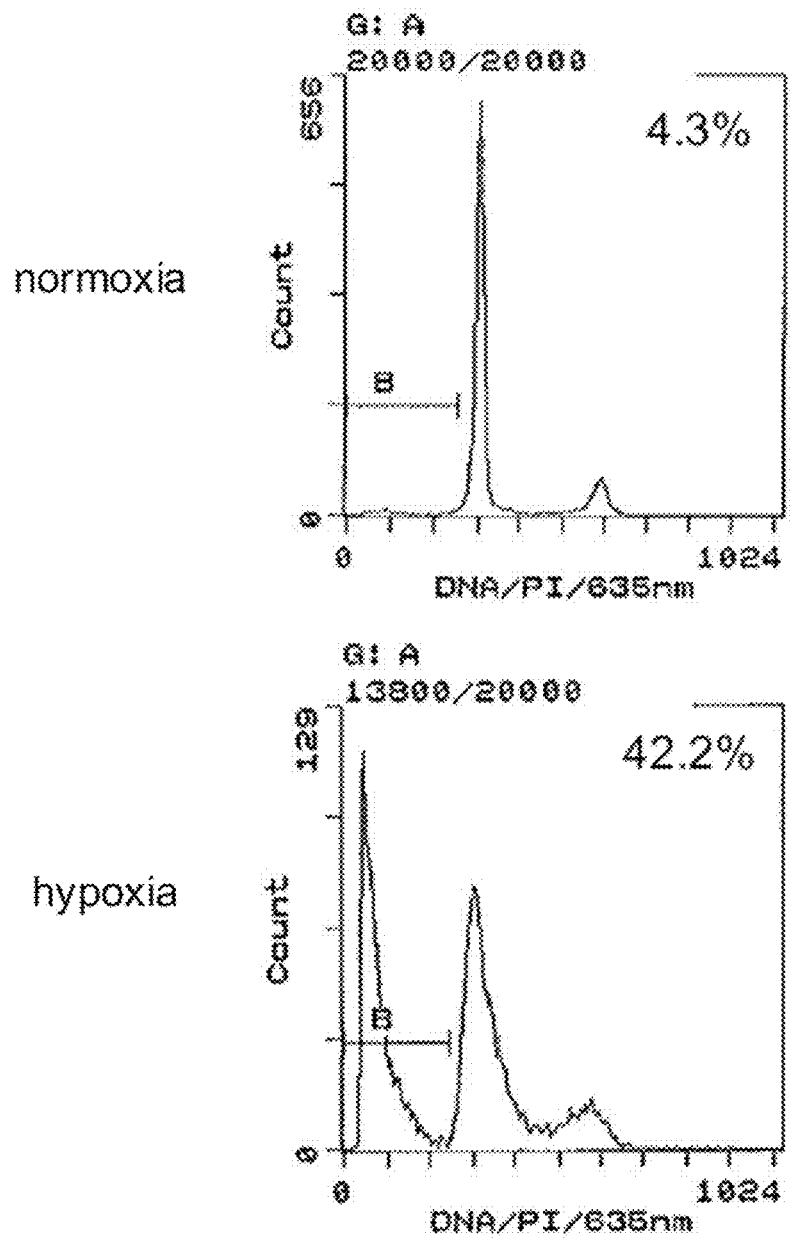
Figure 9:
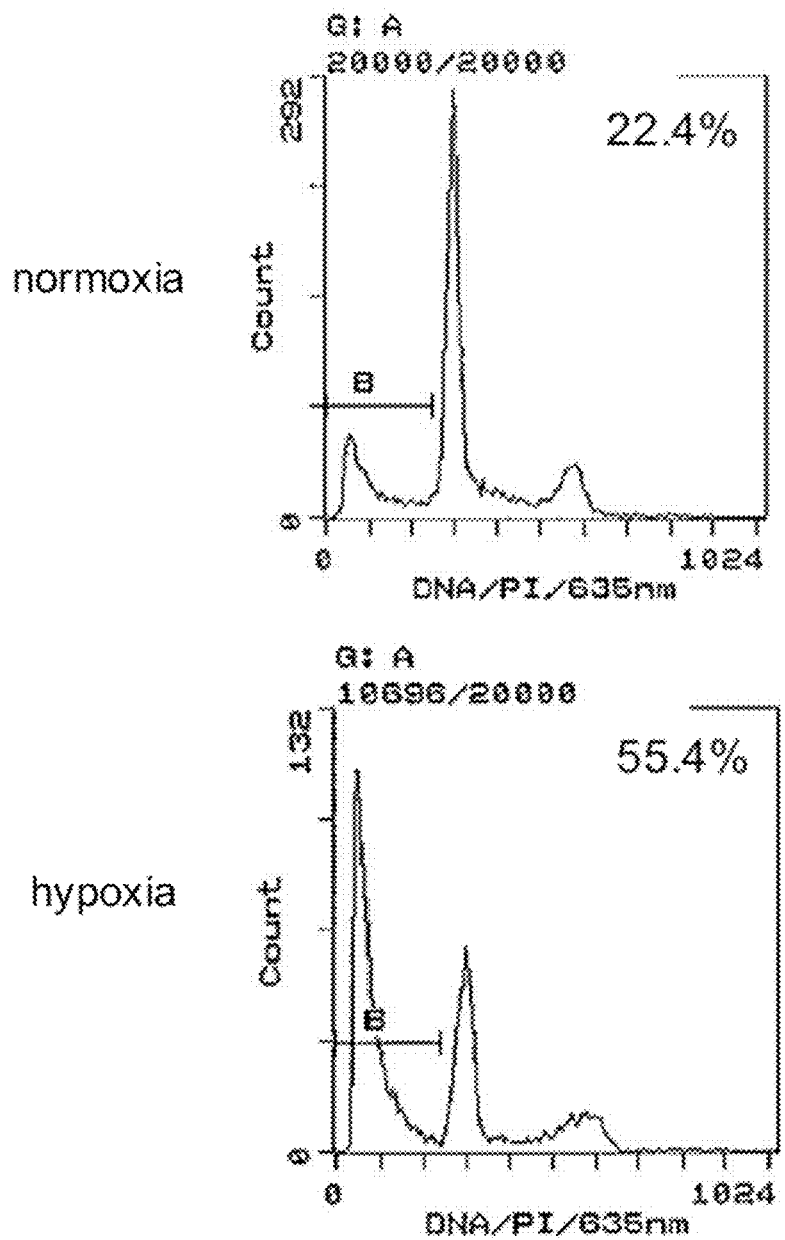
Figure 9:
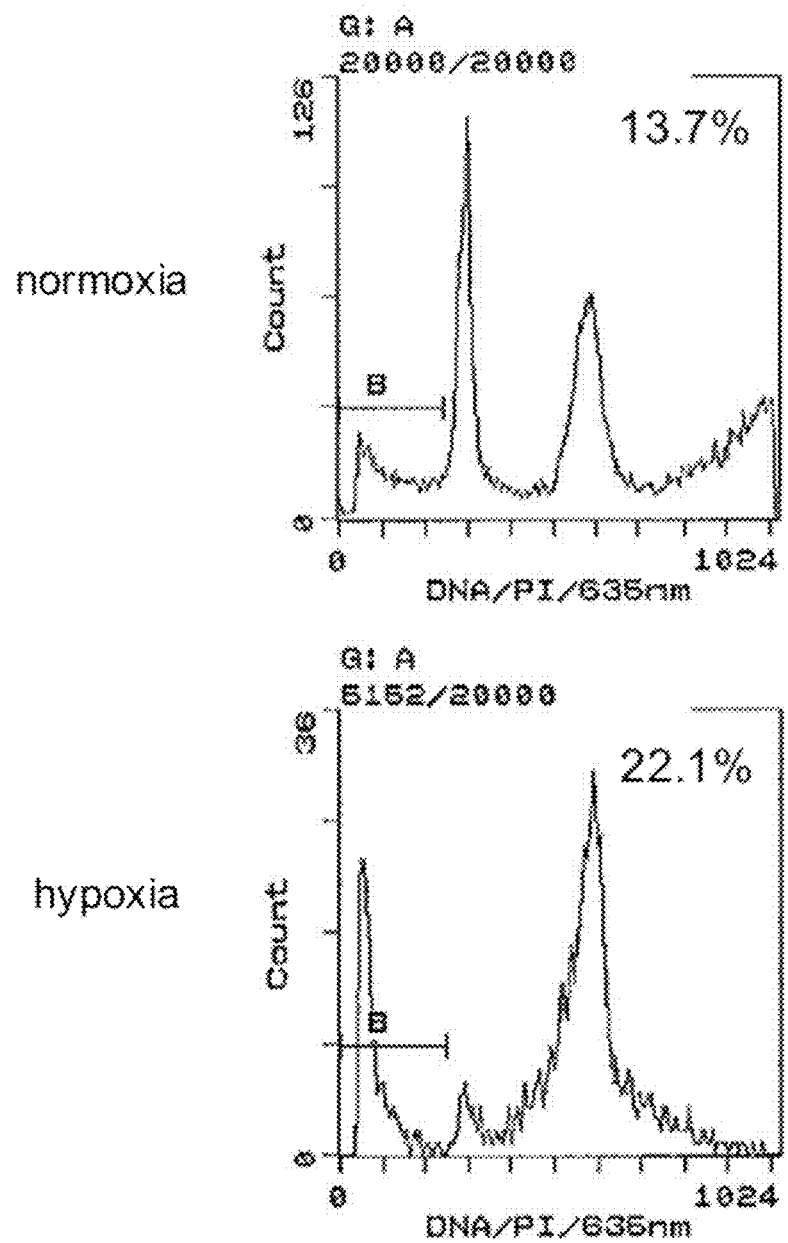
Figure 9:
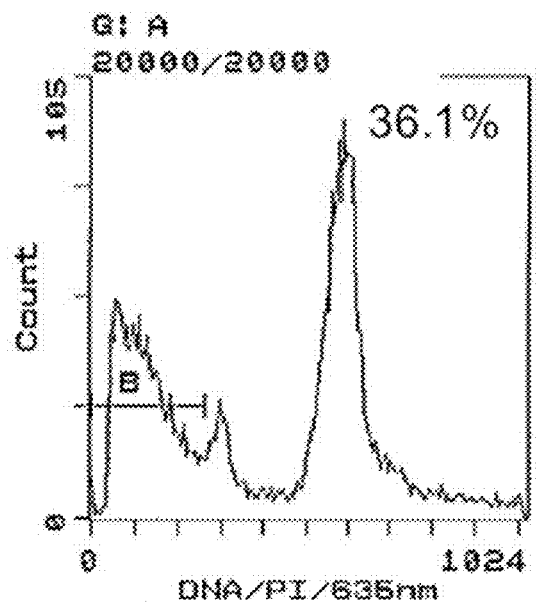
Figure 9:
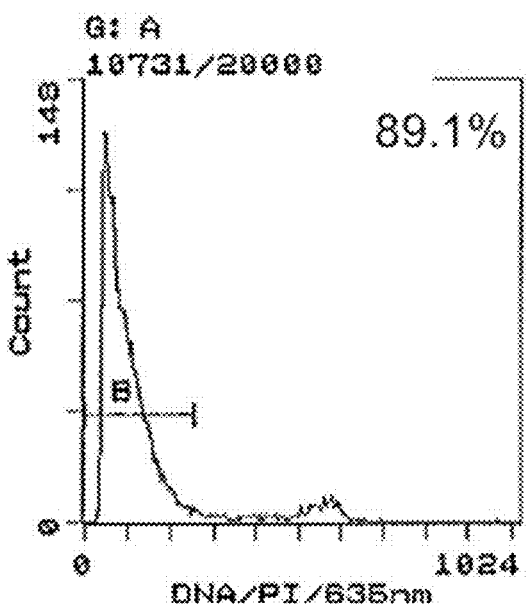
Figure 9:
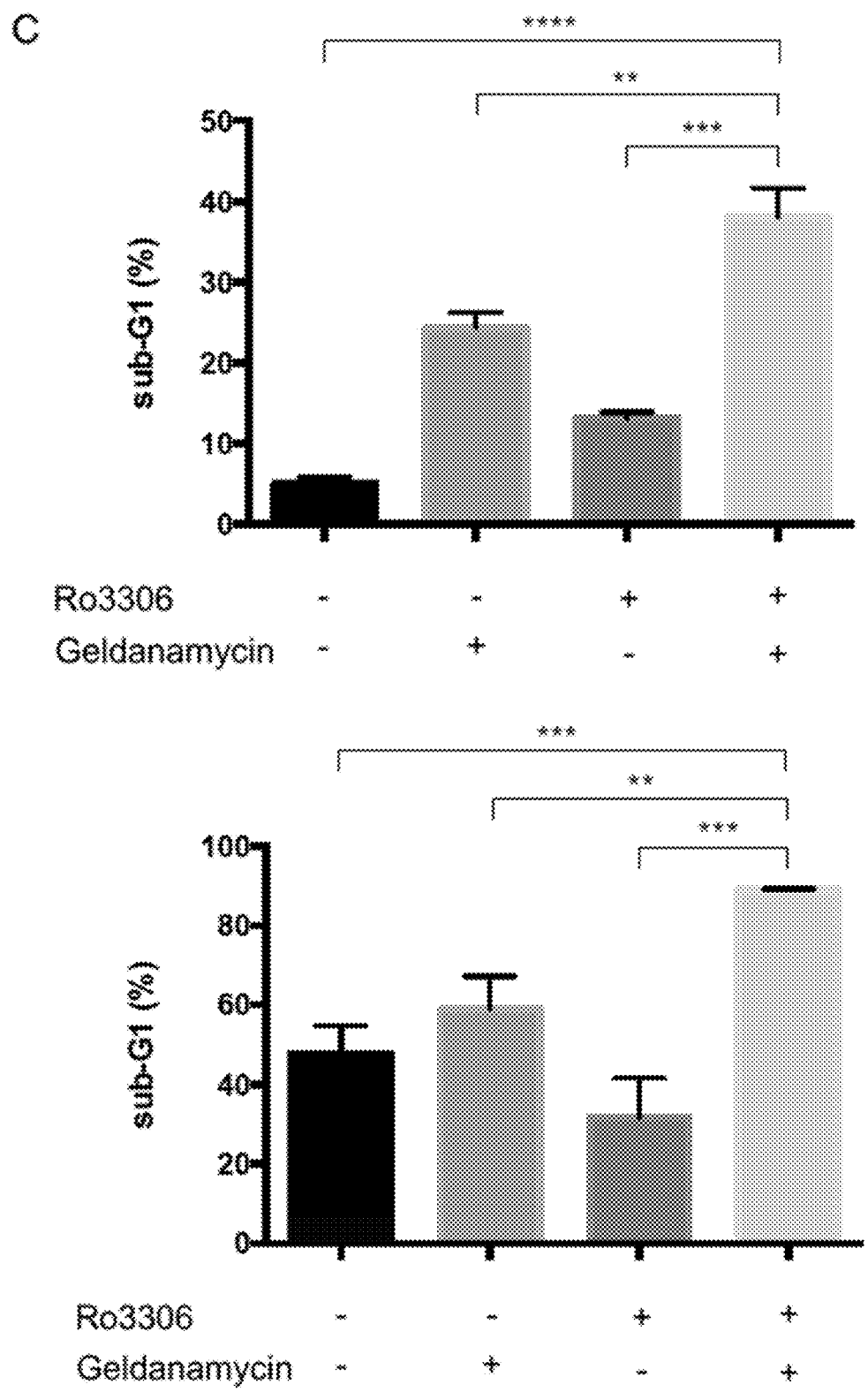
Figure 9:
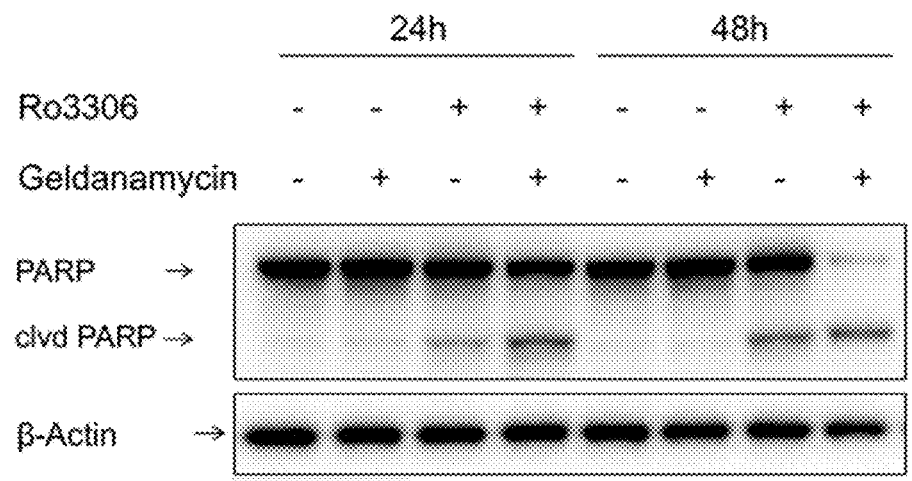
Figure 9:
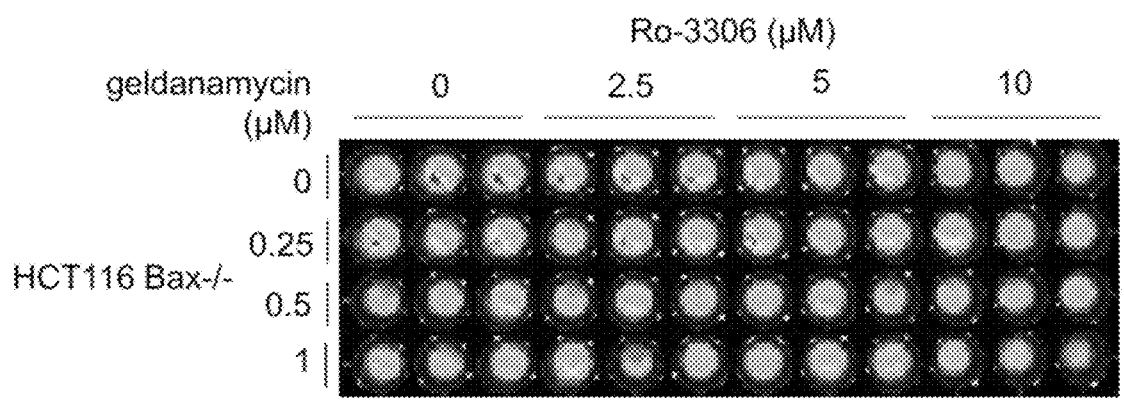

Ro-3306 and geldanamycin synergistically inhibit HCT116 cell viability through induction of apoptosis (see, FIG. 9, Panels A, B, C, D, and E). In normoxia (see, Panel A) or hypoxia (see, Panel B), cells were treated with Ro-3306 and geldanamycin at the indicated concentrations for (Panel A) 48 hours or (Panel B) 72 hours. Sub-G1 analysis was carried out by flow cytometry of cells treated with Ro-3306 at 10 μM and geldanamycin at 1 μM under normoxia for 48 hours or under hypoxia for 72 hours (see, Panel C). A Western blot of PARP cleavage in cells treated with Ro-3306 or geldanamycin or both was also carried out (see, Panel D). CellTiter-Glo analysis of cell viability in HCT116Bax$^{-/-}$ cells treated at the indicated concentrations under normoxia for 48 hours was also carried out (see, Panel E).

Figure 10:
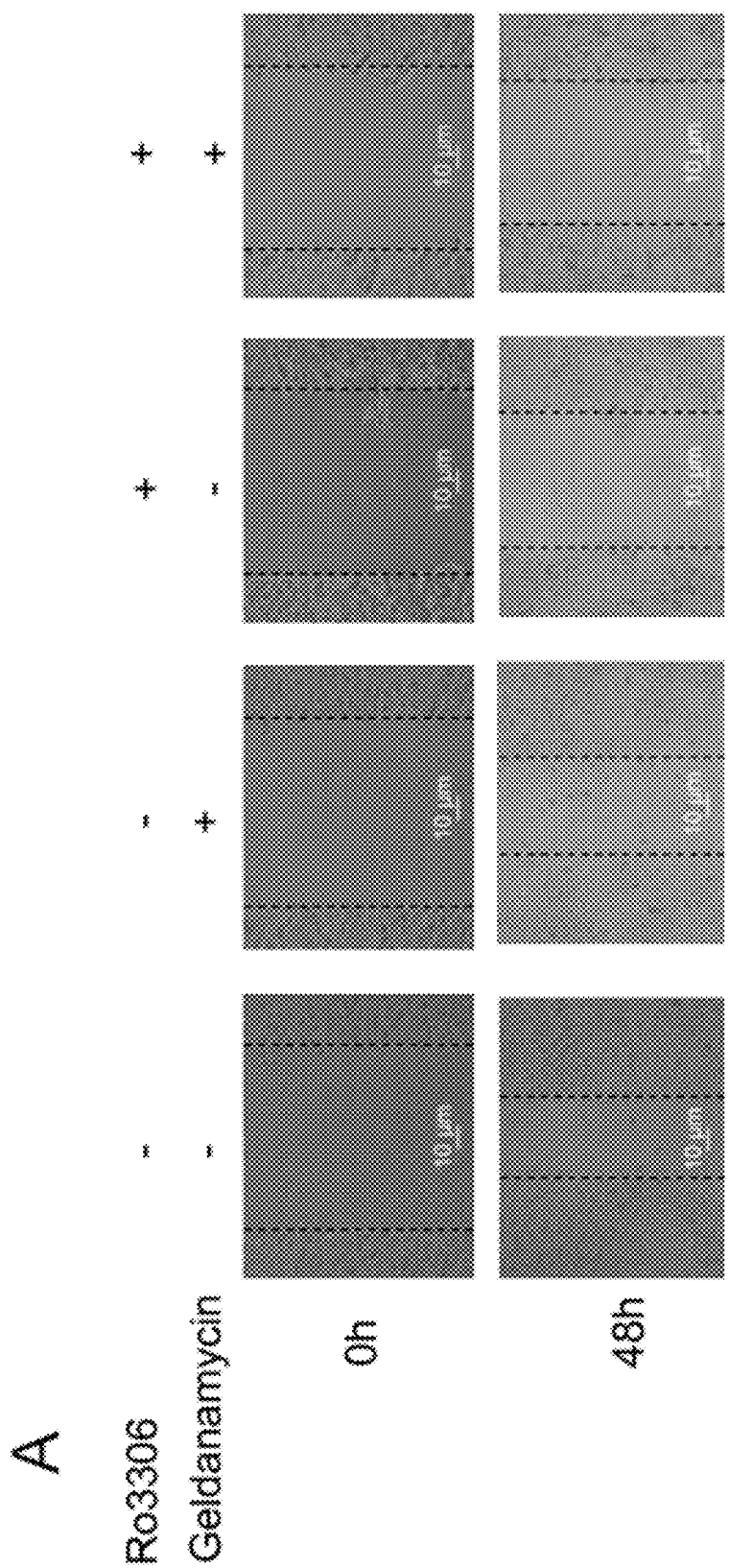
FIG. 10 (Panel A) shows dual inhibition of CDK1 and HSP90 suppresses cell migration; (Panel A) scratch assay for HCT116 cells under normoxia for 48 hours; gap ratio refers to the ratio of gap width at 48 hours versus at 0 hours; cells were treated with Z-VAD caspase inhibitor to prevent cell death; n=3.
Figure 10:
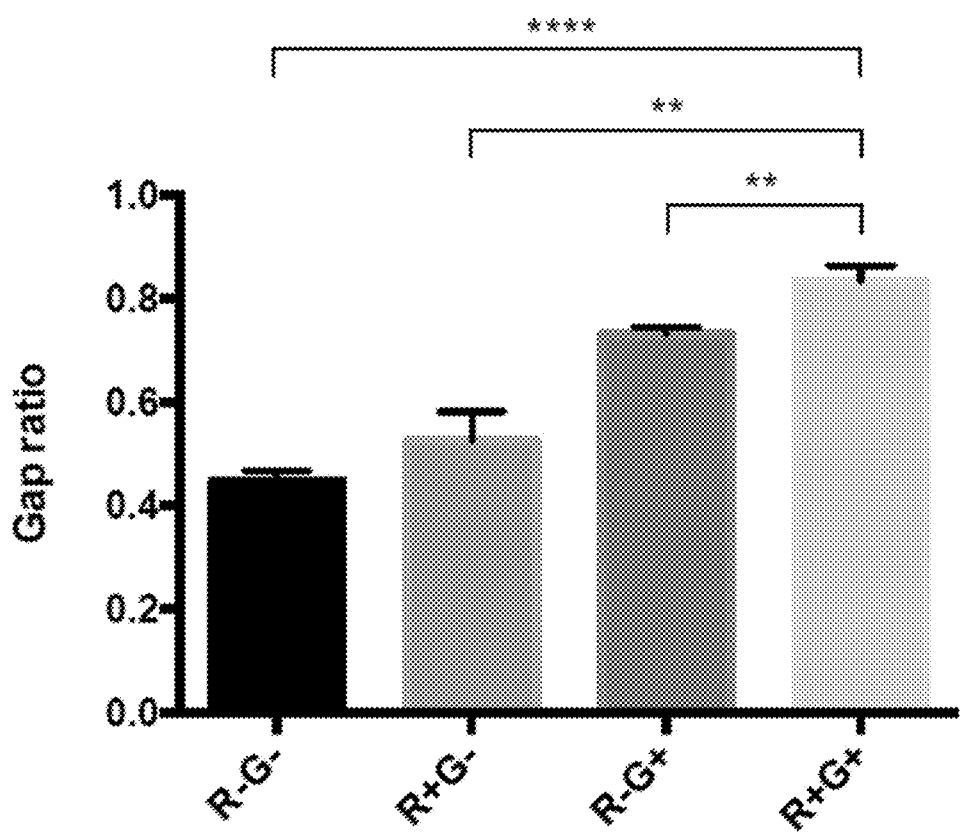

Dual inhibition of CDK1 and HSP90 suppresses cell migration (see, FIG. 10, Panel A). A scratch assay for HCT116 cells under normoxia for 48 hours was carried out. The gap ratio refers to the ratio of gap width at 48 hours versus at 0 hours. Cells were treated with Z-VAD caspase inhibitor to prevent cell death (n=3).

Figure 11:
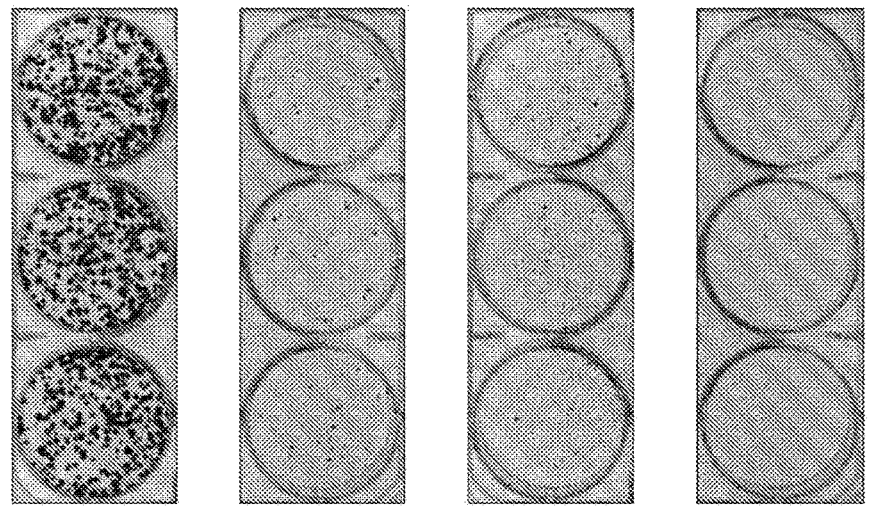
FIG. 11 (Panels A and B) shows that combination treatment inhibits colony formation in HCT116 cells; (Panel A) in normoxia or (Panel B) in hypoxia, HCT116 cells were treated at indicated combination treatments for 72 hours; reagent-containing media were replaced with regular culture media, and cells were allowed to grow and form colonies for 1 week.
Figure 11:
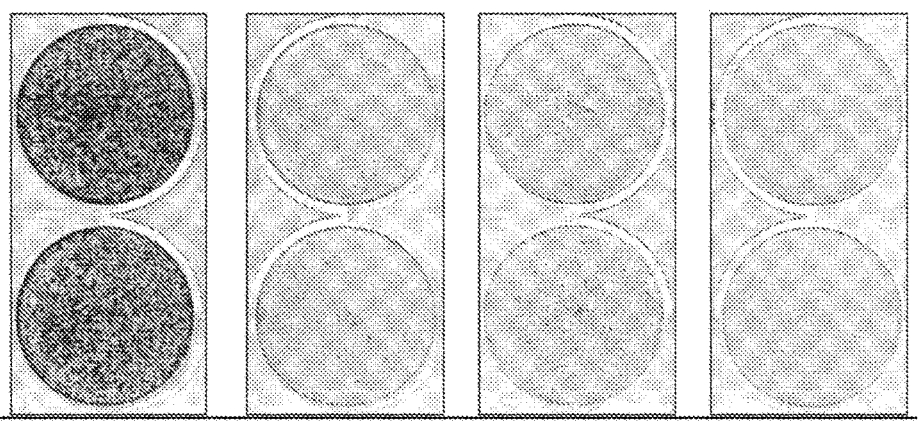

Combination treatment inhibits colony formation in HCT116 cells (see, FIG. 11, Panels A and B). In normoxia (see, Panel A) or in hypoxia (Panel B), HCT116 cells were treated at the indicated combination treatments for 72 hours. Reagent-containing media were replaced with regular culture media, and cells were allowed to grow and form colonies for 1 week.

Figure 12:
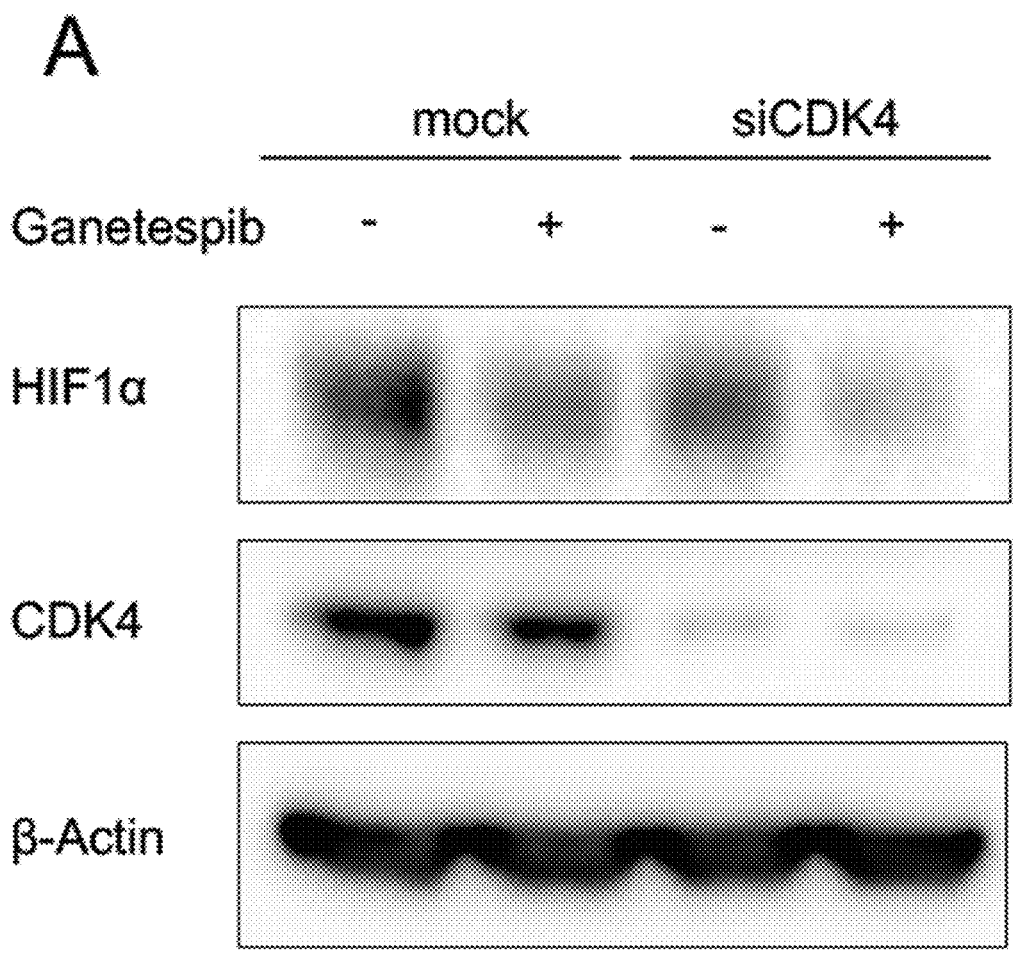
FIG. 12 (Panels A, B, C, D, and E) show dual inhibition of CDK4 and HSP90 similarly reduces HIF1α and inhibits cell viability; (Panel A) HCT116 cells were treated with DMSO or ganetespib after 48 hours knockdown of CDK4; (Panels B and C) CDK4 inhibitor palbociclib and HSP90 inhibitor ganetespib synergistically inhibit the viability of SW480 cells in (Panel B) normoxia and (Panel C) hypoxia; (Panel D) sub-G1 analysis by flow cytometry for HCT116 cells treated with indicated combinations (ganetespib at 0.04 μM; palbocilib at 10 μM) for 48 hours; (Panel E) scratch assay for HT29 cells under $CoCl_2$-induced hypoxia for 72 hours.
Figure 12:
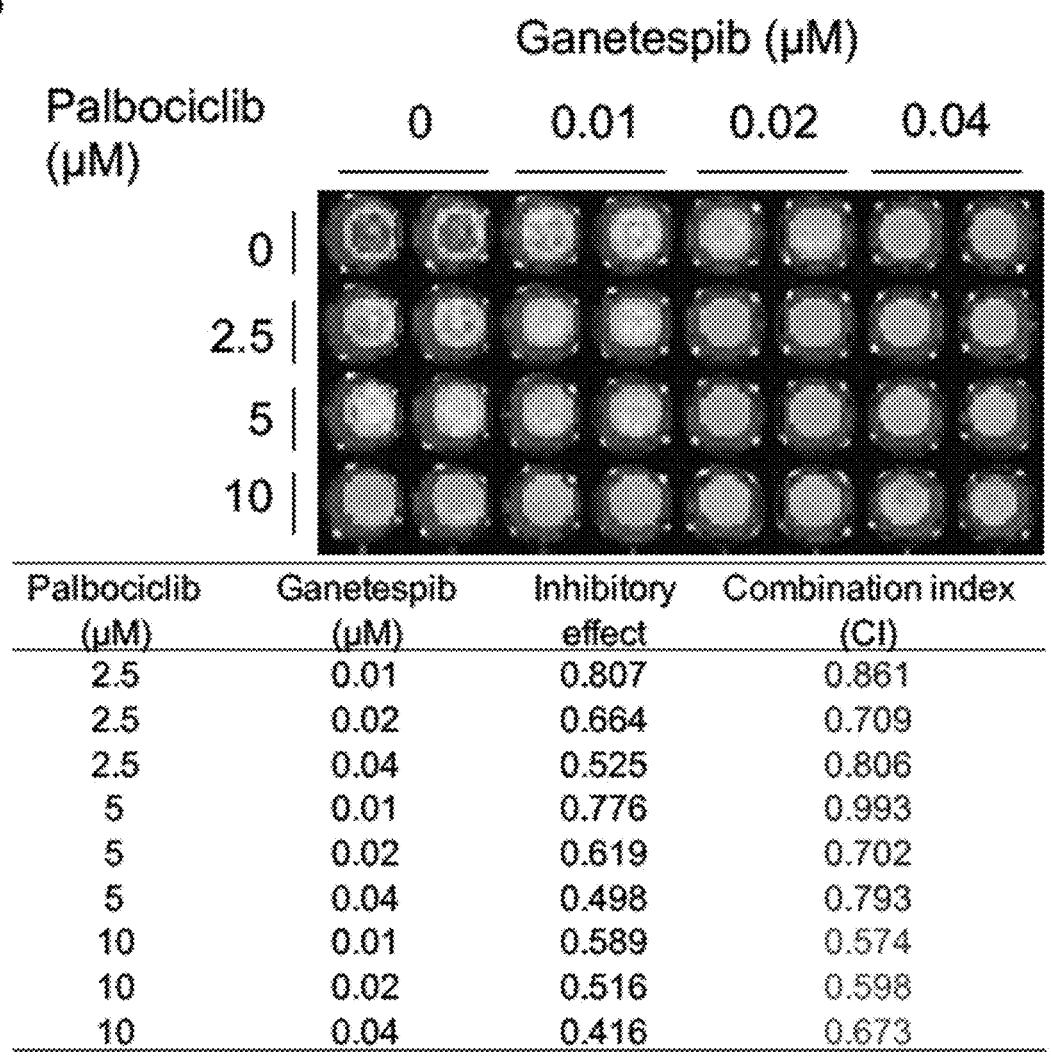
Figure 12:
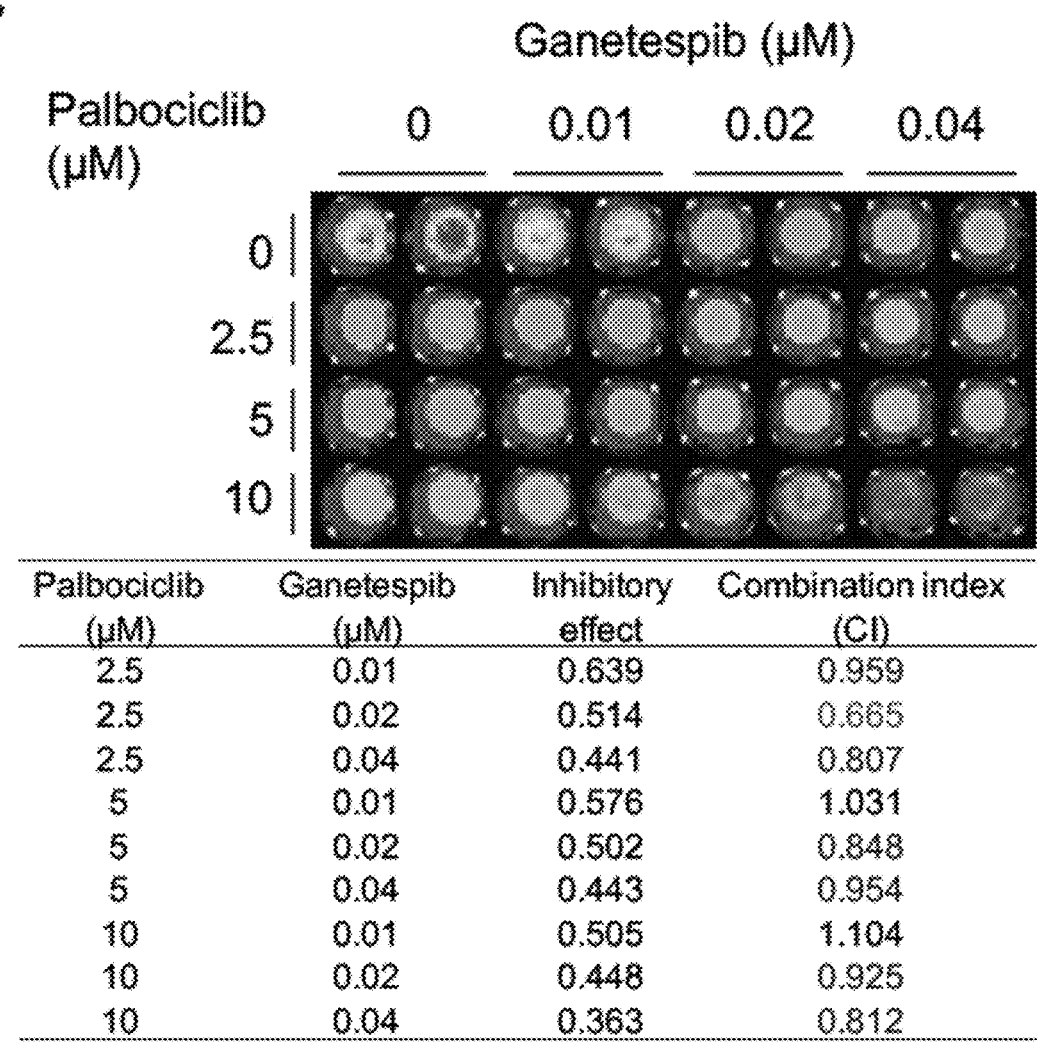
Figure 12:
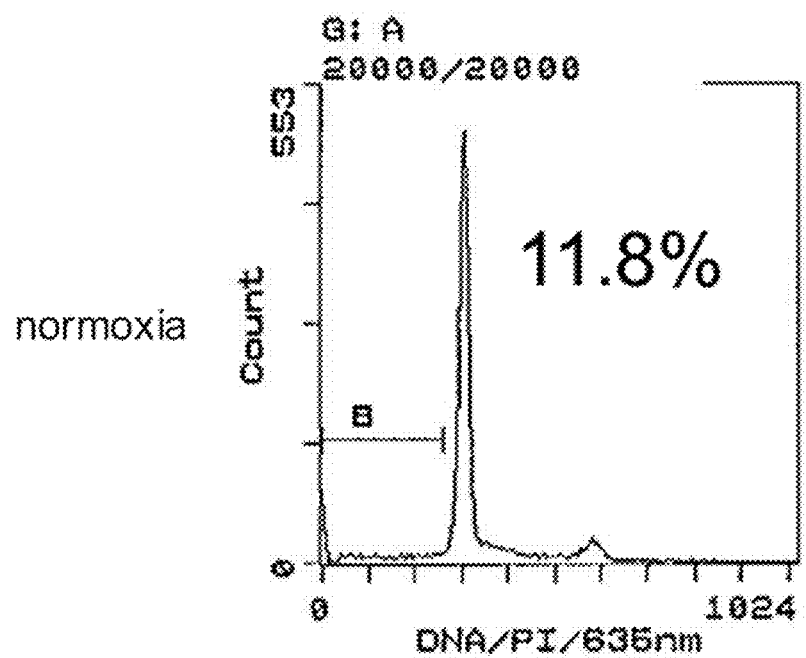
Figure 12:
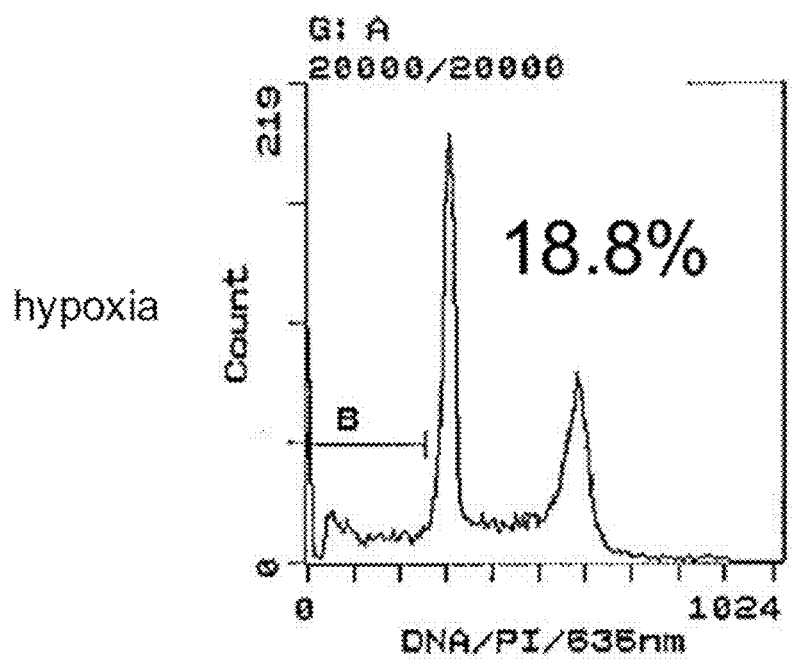
Figure 12:
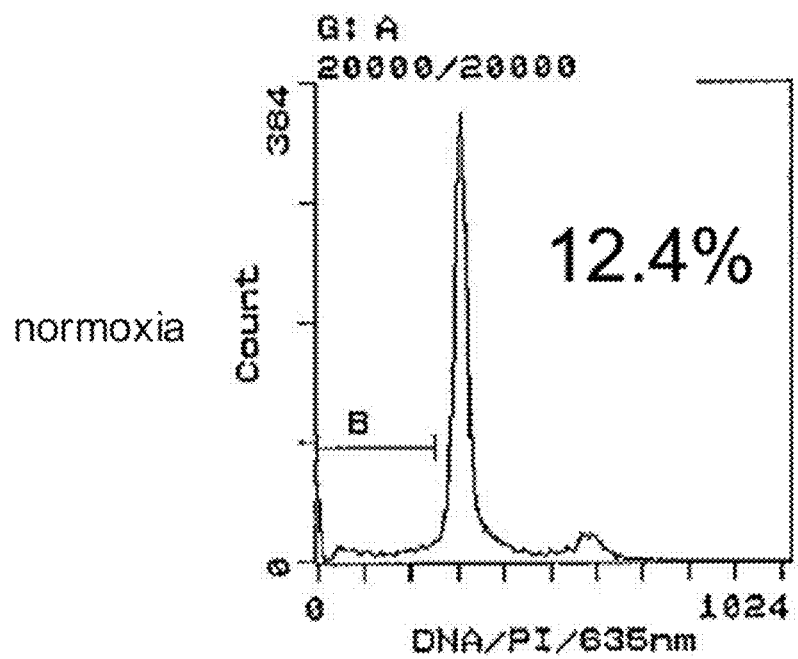
Figure 12:
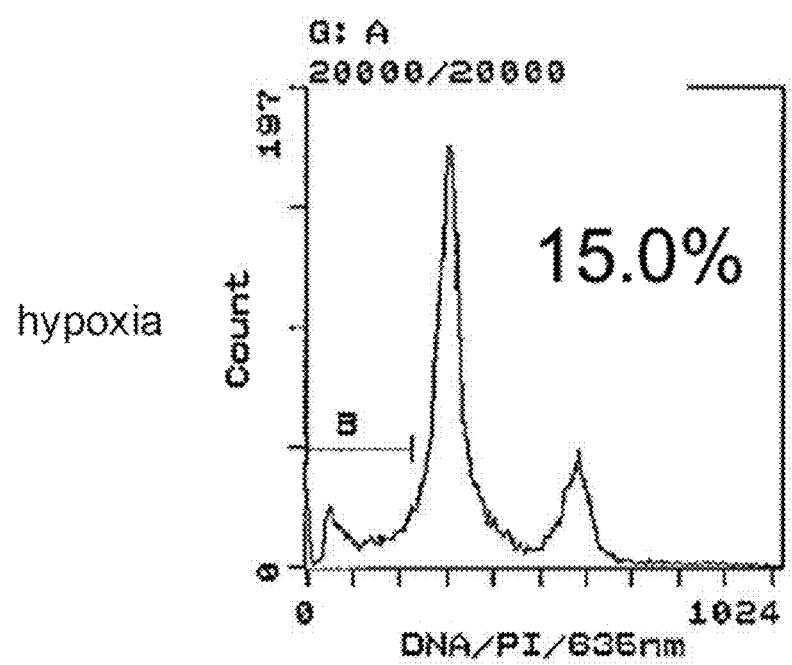
Figure 12:
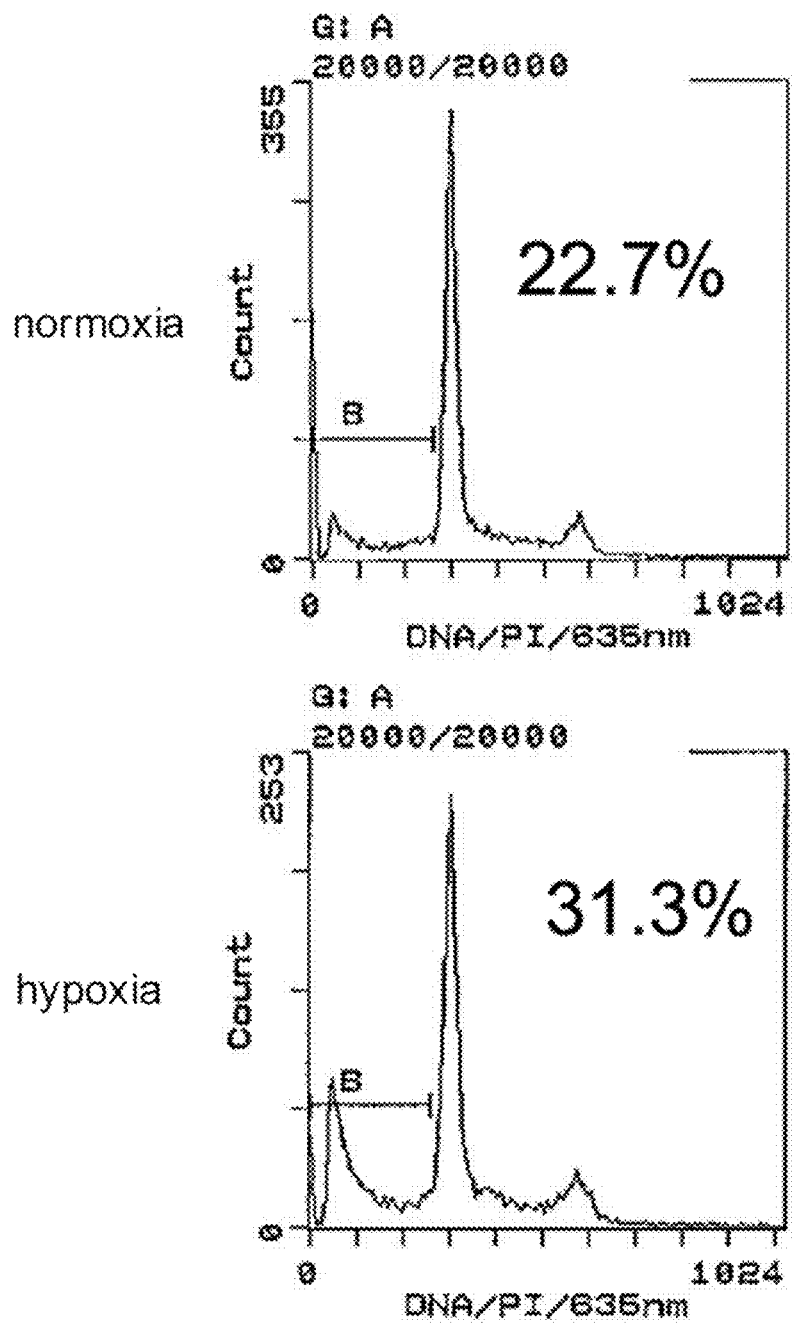
Figure 12:
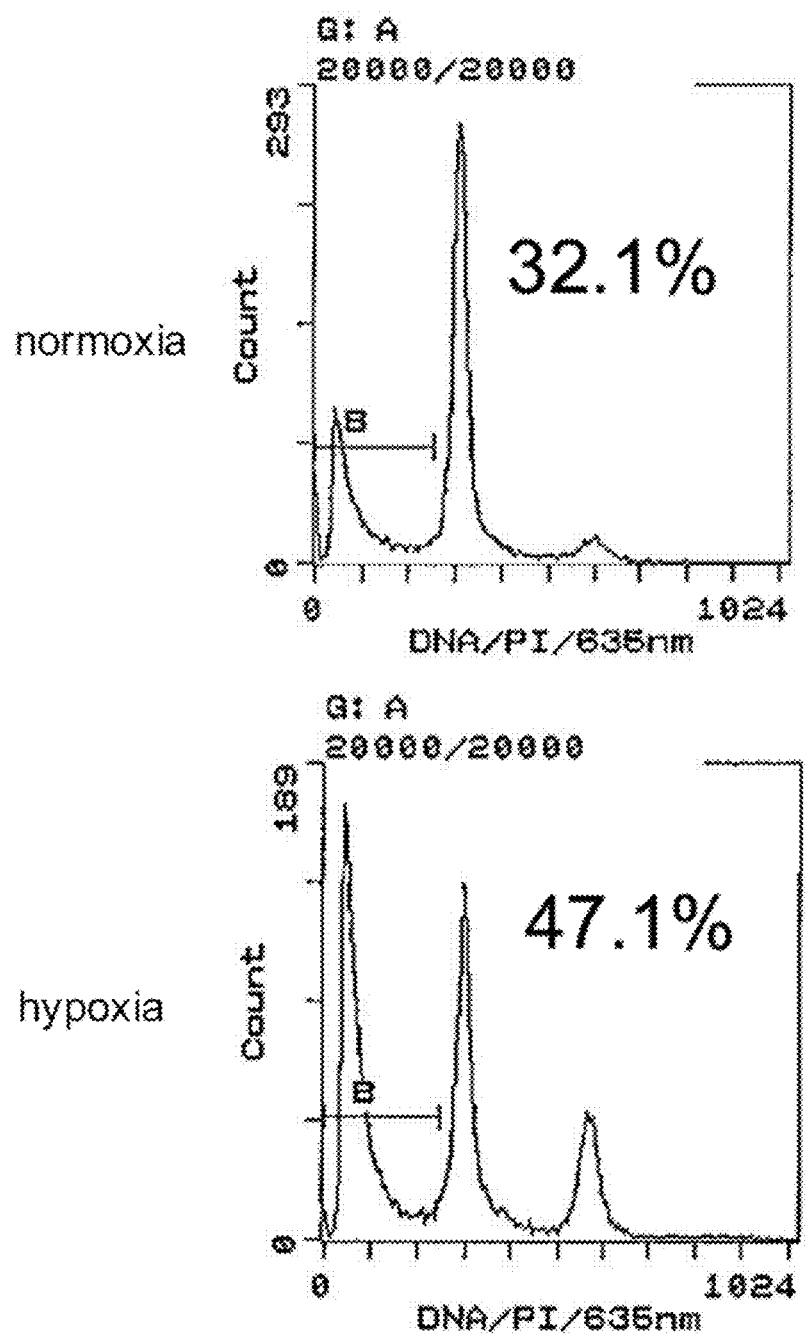
Figure 12:
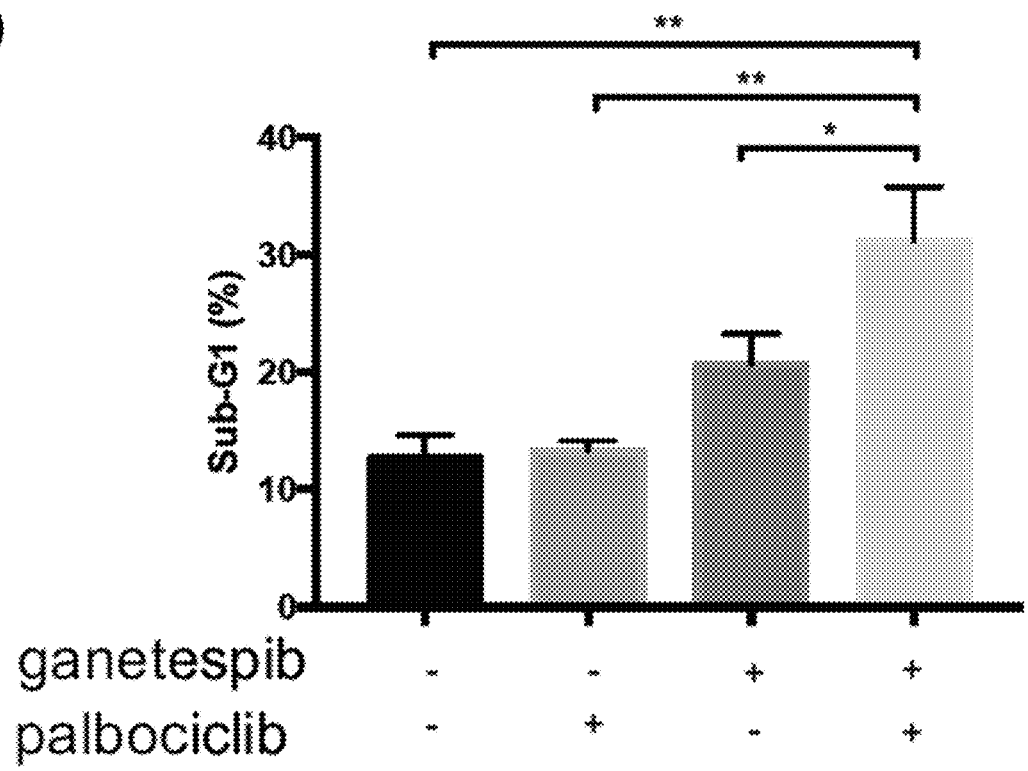
Figure 12:
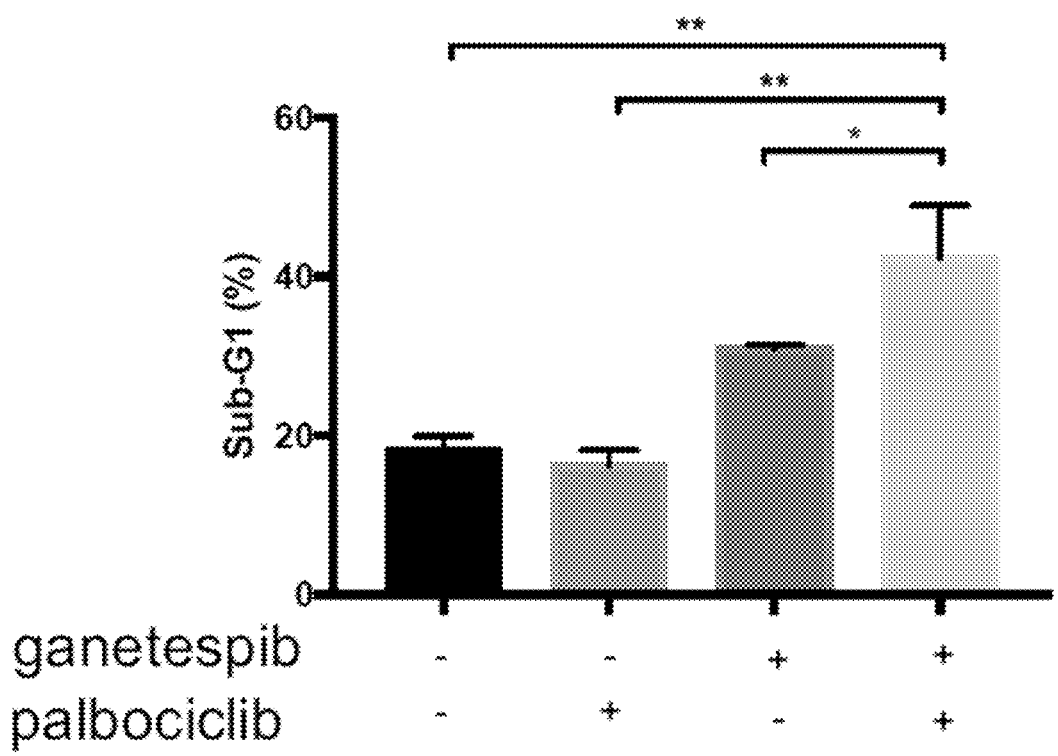
Figure 12:
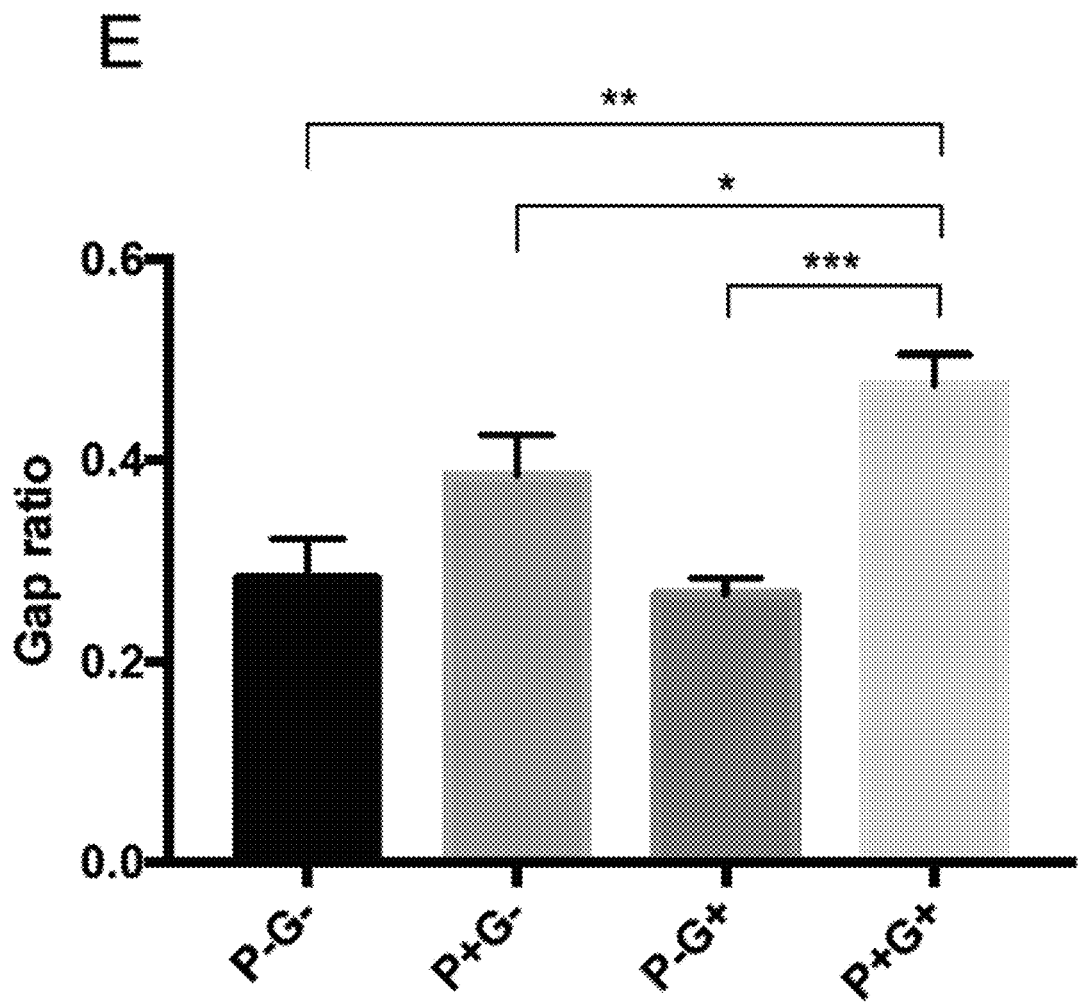

Dual inhibition of CDK4 and HSP90 similarly reduces HIF1α and inhibits cell viability (see, FIG. 12, Panels A, B, C, D, and E). HCT116 cells were treated with DMSO or ganetespib after 48 hours knockdown of CDK4 (see, Panel A). The CDK4 inhibitor palbociclib and the HSP90 inhibitor ganetespib synergistically inhibit the viability of SW480 cells in normoxia (see, Panel B) and hypoxia (Panel C). Sub-G1 analysis was carried out by flow cytometry for HCT116 cells treated with indicated combinations (ganetespib at 0.04 M; palbocilib at 10 μM) for 48 hours (see, Panel D). A scratch assay for HT29 cells under $CoCl_2$-induced hypoxia for 72 hours was also performed (see, Panel E).

Figure 13:
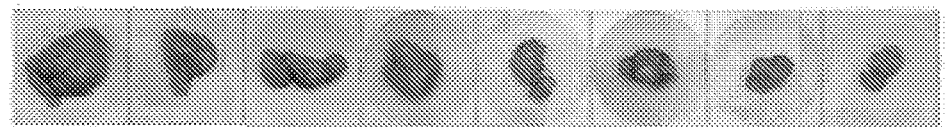
FIG. 13 (Panels A, B, C, D, and E) show that combination treatment with palbociclib and ganetespib inhibits tumor growth in vivo; (Panel A) tumors excised from HT29 xenografts in nude mice; (Panel B) tumor weight quantification of excised tumors; (Panel C) relative tumor volume measured over time; (Panel D) body weight of mice in different treatment groups; and (Panel E) combination treatment inhibits microvessel formation in tumors in vivo.
Figure 13:
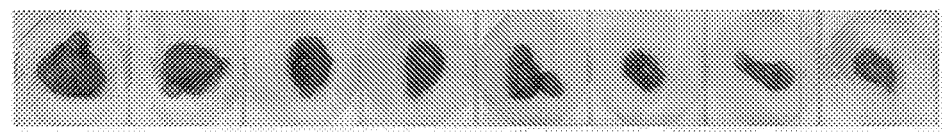
Figure 13:
Figure 13:
Figure 13:
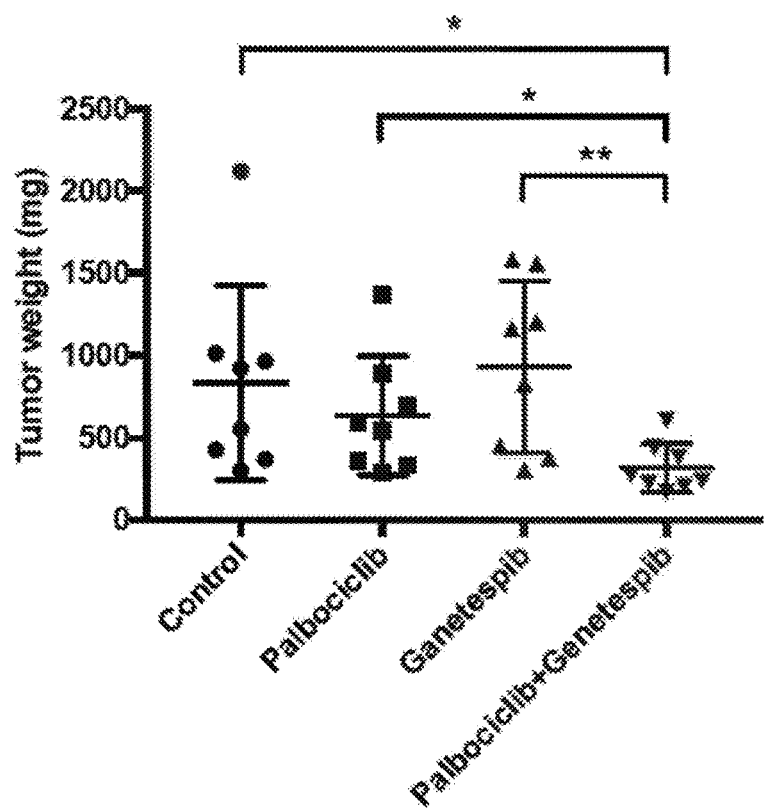
Figure 13:
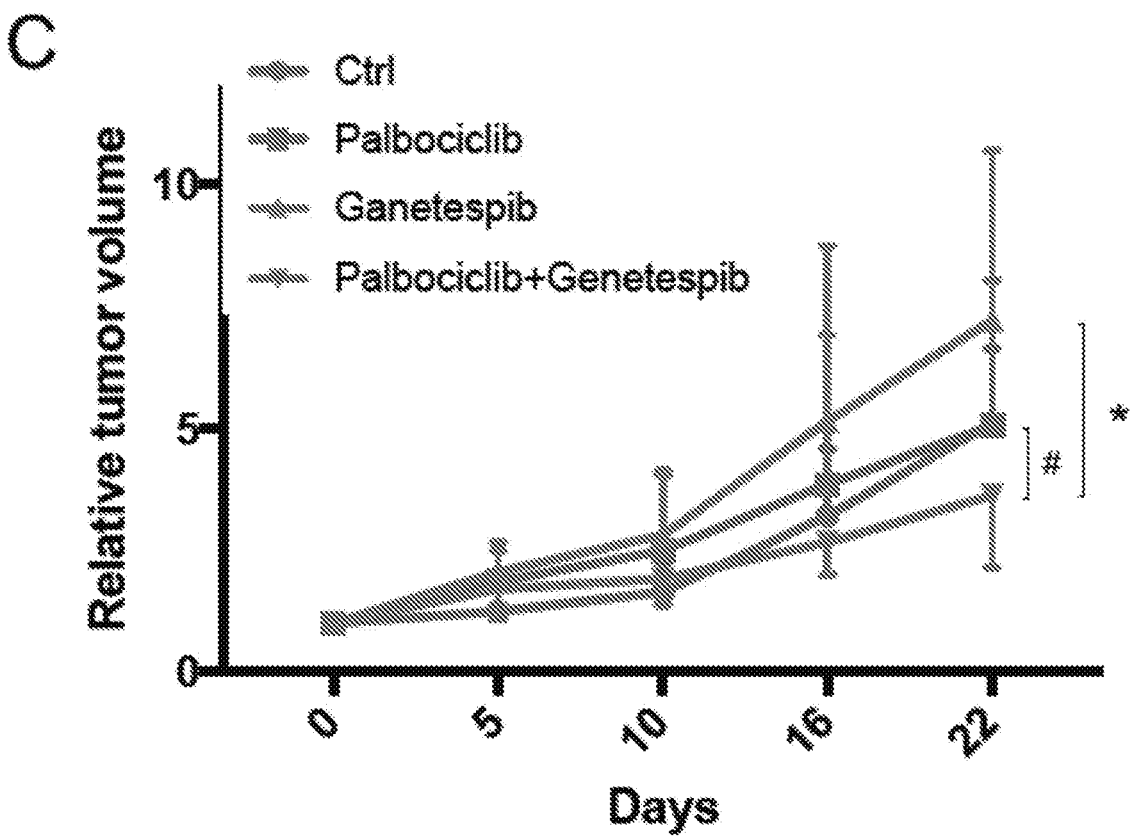
Figure 13:
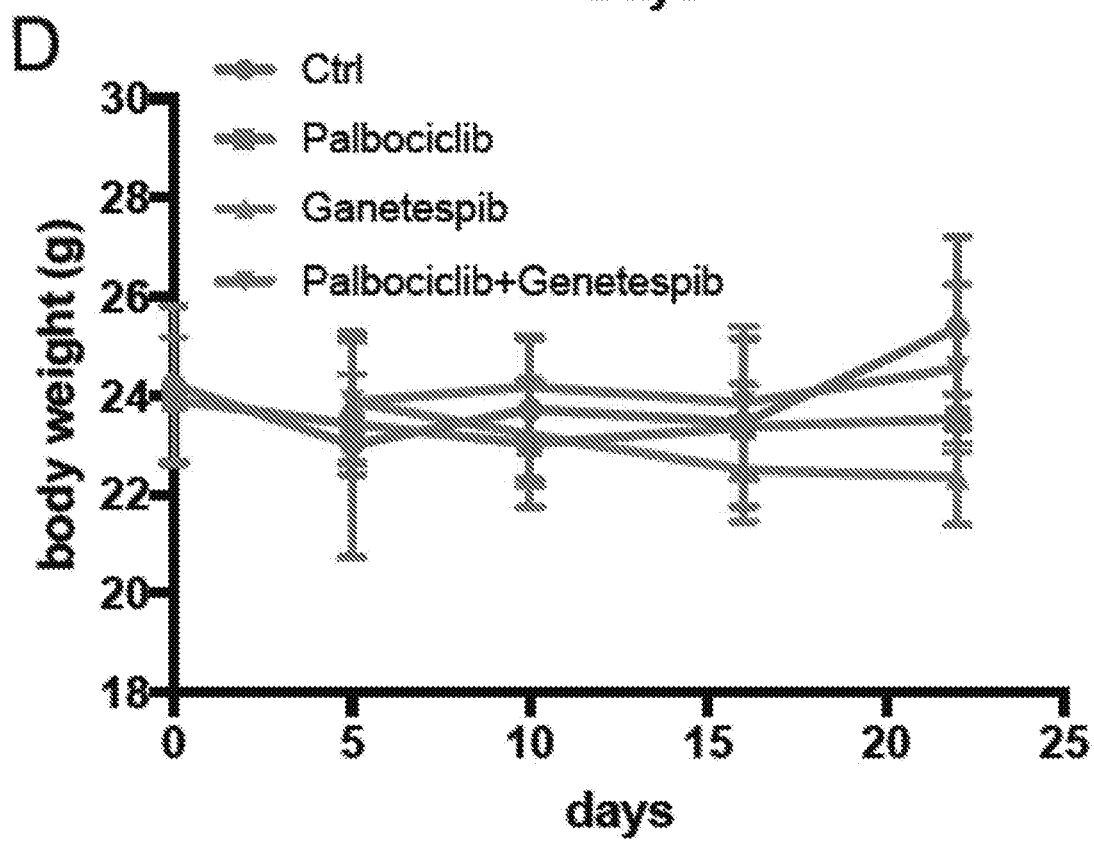
Figure 13:
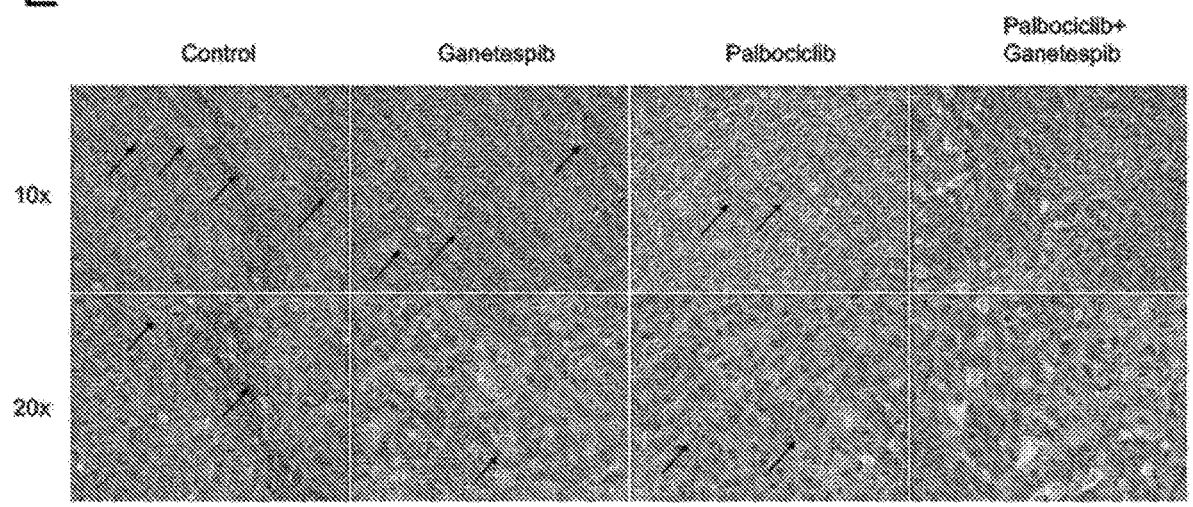

Combination treatment with palbociclib and ganetespib inhibits tumor growth in vivo (see, FIG. 13, Panels A, B, C, D, and E). Tumors were excised from HT29 xenografts in nude mice (see, Panel A). Tumor weight of excised tumors was quantified (see, Panel B). Relative tumor volume was measured over time (see, Panel C). The body weight of mice in different treatment groups was analyzed (see, Panel D). Combination treatment inhibited microvessel formation in tumors in vivo (see, Panel E).

Figure 14:
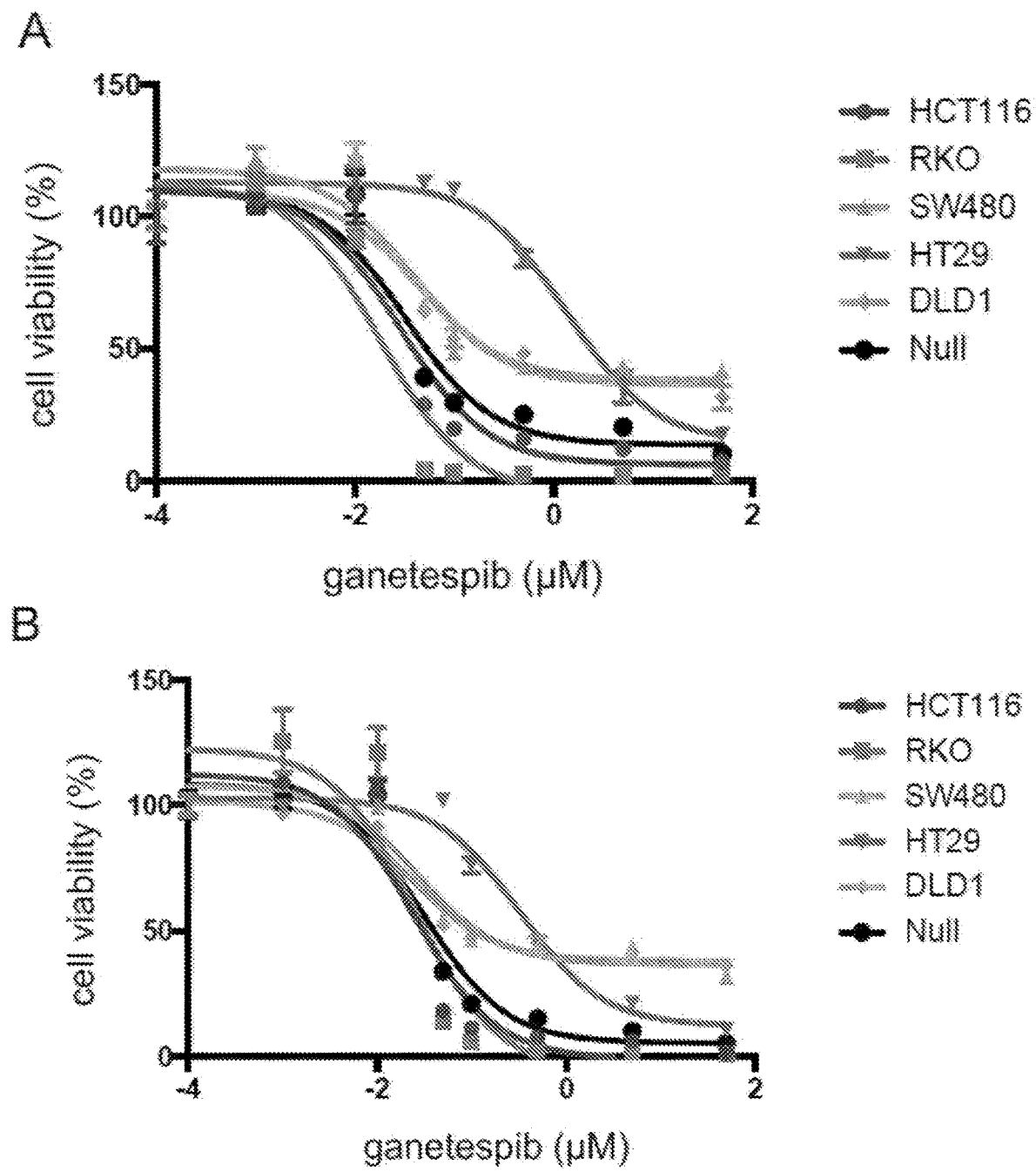
FIG. 14 (Panels A and B) show dose response curves of ganetespib in colorectal cancer cell lines; (Panel A) in normoxia or (Panel B) in hypoxia, cells were treated with increasing doses of ganetespib for 72 hours.

Dose response curves of ganetespib were obtained for colorectal cancer cell lines (see, FIG. 14, Panels A and B). In normoxia (see, Panel A) or in hypoxia (Panel B), cells were treated with increasing doses of ganetespib for 72 hours.

Figure 15:
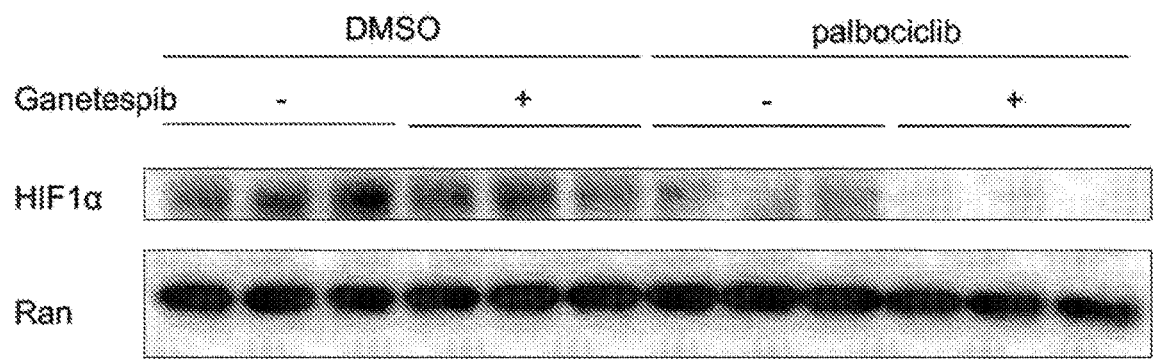
FIG. 15 (Panels A and B) show dual inhibition of CDK4 and HSP90 robustly decreases the levels of HIF1α in other cancer cell types; (Panel A) T98G cells were treated with palbociclib or ganetespib or the combination of both in hypoxia for 6 hours; (Panel B) PC3 cells were treated with ganetespib for 6 hours under hypoxia after 48 hours knockdown of CDK4.
Figure 15:
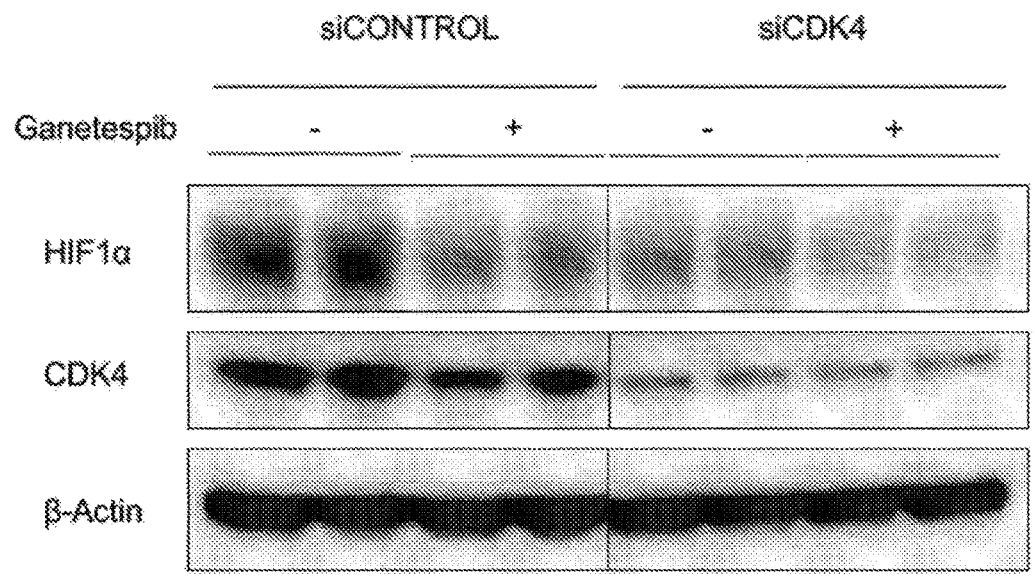
Figure 16:
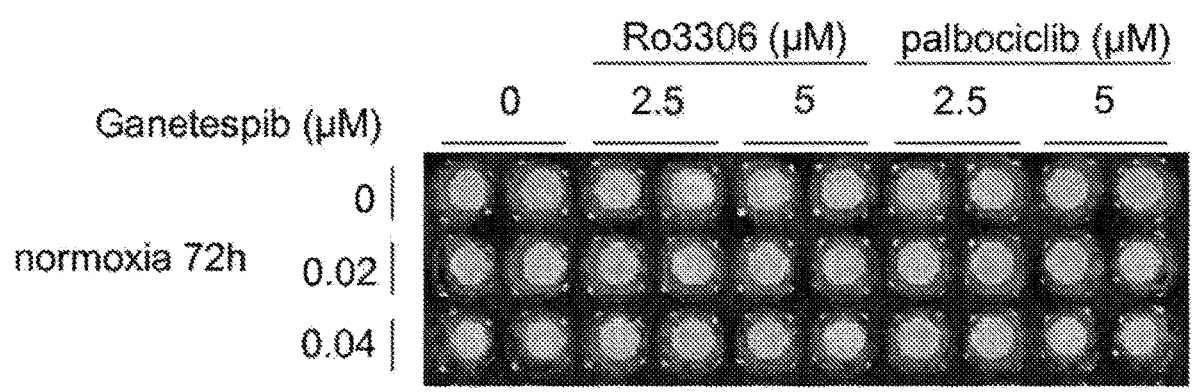
FIG. 16 shows that a similar combination of palbociclib and ganetespib does not remarkably induce cell death in WI38 normal cells in normoxia.

Dual inhibition of CDK4 and HSP90 robustly decreased the levels of HIF1α in other cancer cell types (see, FIG. 15, Panels A and B). T98G cells were treated with palbociclib or ganetespib or the combination of both in hypoxia for 6 hours (see, Panel A). PC3 cells were treated with ganetespib for 6 hours under hypoxia after 48 hours knockdown of CDK4 (see, Panel B). A similar combination of palbociclib and ganetespib does not remarkably induce cell death in WI38 normal cells in normoxia (see, FIG. 16).

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A method of treating lung cancer, breast cancer, colon cancer, renal cancer, glioblastoma, or colorectal cancer in a subject in need thereof, comprising:
   administering a CDK inhibitor to the subject; and
   administering an HSP90 inhibitor to the subject;
   provided that both RO-3306 and geldanamycin are not administered to the subject.

2. The method of claim 1, wherein the CDK inhibitor is Kenpaullone, PKC-412, Butyrolactone I, Cdk1/5 Inhibitor, Flavopiridol, N9-Isopropyl-olomoucine, Indirubin-3'-monoxime, NU2058, Olomoucine II, 9-Cyanopaullone, 5-Iodo-Indirubin-3'-monoxime, NU6102, Oxindole I, SU 9516, Roscovitine, RO-3306, 10Z-Hymenialdisine, AZD 5438, AT7519, Dinaciclib, R547, CGP 74514A, SNS-032 (BMS-387032), BMS-265246, JNJ-7706621, PHA-793887, P276-00, PHA-767491, Milciclib (PHA-848125), NU6027, LDC000067, ribociclib, palbociclib, or abemaciclib.

3. The method of claim 2, wherein the CDK inhibitor is Roscovitine, palbociclib, or abemaciclib.

4. The method of claim 1, wherein the HSP90 inhibitor is 17-AAG (Tanespimycin), Luminespib (AUY-922, NVP-AUY922), 17-DMAG, (Alvespimycin) HCl, Ganetespib (STA-9090), Apoptozole, BIIB021, Onalespib (AT13387), NVP-BEP800, geldanamycin, SNX-2112 (PF-04928473), PF-04929113 (SNX-5422), KW-2478, XL888, NMS-E973, PU-H71, DEB10-0932, DS-2248, WC-3100, TAS-116, Radicicol, or gamitrinib.

5. The method of claim 4, wherein the HSP90 inhibitor is Ganetespib (STA-9090) or Onalespib (AT13387).

6. The method of claim 1, wherein the CDK inhibitor is Roscovitine and the HSP90 inhibitor is Ganetespib (STA-9090), the CDK inhibitor is palbociclib and the HSP90 inhibitor is Ganetespib (STA-9090), the CDK inhibitor is palbociclib and the HSP90 inhibitor is Onalespib (AT13387), the CDK inhibitor is abemaciclib and the HSP90 inhibitor is Ganetespib (STA-9090), or the CDK inhibitor is abemaciclib and the HSP90 inhibitor is Onalespib (AT13387).

7. The method of claim 1, wherein the CDK inhibitor and the HSP90 inhibitor are both present in a single pharmaceutical composition.

8. The method of claim 2, wherein the CDK inhibitor is Roscovitine.

9. The method of claim 2, wherein the CDK inhibitor is palbociclib.

10. The method of claim 2, wherein the CDK inhibitor is abemaciclib.

11. The method of claim 4, wherein the HSP90 inhibitor is Ganetespib (STA-9090).

12. The method of claim 4, wherein the HSP90 inhibitor is Onalespib (AT13387).

13. The method of claim 1, wherein the CDK inhibitor is Roscovitine and the HSP90 inhibitor is Ganetespib (STA-9090).

14. The method of claim 1, wherein the CDK inhibitor is palbociclib and the HSP90 inhibitor is Ganetespib (STA-9090).

15. The method of claim 1, wherein the CDK inhibitor is palbociclib and the HSP90 inhibitor is Onalespib (AT13387).

16. The method of claim 1, wherein the CDK inhibitor is abemaciclib and the HSP90 inhibitor is Ganetespib (STA-9090).

17. The method of claim 1, wherein the CDK inhibitor is abemaciclib and the HSP90 inhibitor is Onalespib (AT13387).

18. The method of claim 1, wherein the cancer is colon cancer.

19. The method of claim 1, wherein the cancer is glioblastoma.

* * * * *

UNITED STATES PATENT AND TRADEMARK OFFICE
CERTIFICATE OF CORRECTION

PATENT NO. : 10,987,356 B2
APPLICATION NO. : 16/681253
DATED : April 27, 2021
INVENTOR(S) : Shuai Zhao et al.

Page 1 of 1

It is certified that error appears in the above-identified patent and that said Letters Patent is hereby corrected as shown below:

In the Claims

Claim 4, Column 23, Line 13 "WC-3100," should be MPC-3100,

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*